US012158931B2

(12) United States Patent
Ando et al.

(10) Patent No.: US 12,158,931 B2
(45) Date of Patent: Dec. 3, 2024

(54) IDENTIFYING DEVICE AND IDENTIFYING METHOD USING REFLECTED LIGHT FROM A BODY OF A USER IRRADIATED BY PULSED LIGHT

(71) Applicant: Panasonic Intellectual Property Management Co., Ltd., Osaka (JP)

(72) Inventors: Takamasa Ando, Osaka (JP); Tsuguhiro Korenaga, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 177 days.

(21) Appl. No.: 17/088,653

(22) Filed: Nov. 4, 2020

(65) Prior Publication Data

US 2021/0049252 A1 Feb. 18, 2021

Related U.S. Application Data

(63) Continuation of application No. PCT/JP2019/018315, filed on May 8, 2019.

(30) Foreign Application Priority Data

May 30, 2018 (JP) ................... 2018-103301

(51) Int. Cl.
 *G06F 21/32* (2013.01)
 *G01S 17/89* (2020.01)
 (Continued)

(52) U.S. Cl.
 CPC .............. *G06F 21/32* (2013.01); *G01S 17/89* (2013.01); *G06V 10/145* (2022.01);
 (Continued)

(58) Field of Classification Search
 CPC .... G06F 21/32; G06V 40/13; G06V 40/1341; G01S 17/89; H04N 5/2256
 See application file for complete search history.

(56) References Cited

U.S. PATENT DOCUMENTS 6,714,666 B1 3/2004 Morimura et al.
8,285,010 B2 * 10/2012 Rowe ................. G06V 40/1324
382/117
(Continued)

FOREIGN PATENT DOCUMENTS

CN 103370727 A 10/2013
JP 2001-324303 A 11/2001
(Continued)

OTHER PUBLICATIONS

International Search Report of PCT application No. PCT/JP2019/018315 dated Aug. 6, 2019.
(Continued)

*Primary Examiner* — James T Boylan
(74) *Attorney, Agent, or Firm* — Rimon P.C.

(57) ABSTRACT

An identifying device includes a light source, an image sensor, a memory that stores biometric data indicating a feature of a body of a user, and a processor. The processor causes the light source to emit pulsed light having a pulse duration of more than or equal to 0.2 ns and less than or equal to 1 μs to illuminate the user with the pulsed light, causes the image sensor to detect at least part of reflected pulsed light that returns from the user and to output a signal corresponding to two-dimensional distribution of an intensity of the at least part of the reflected pulsed light, and verifies the signal against the biometric data to identify the user.

10 Claims, 19 Drawing Sheets

(51) Int. Cl.
  *G06V 10/145* (2022.01)
  *G06V 40/16* (2022.01)
  *G06V 40/70* (2022.01)
  *H04N 23/56* (2023.01)
  *G06V 40/12* (2022.01)
  *G06V 40/13* (2022.01)
  *G06V 40/14* (2022.01)

(52) U.S. Cl.
  CPC .......... *G06V 40/168* (2022.01); *G06V 40/172* (2022.01); *G06V 40/70* (2022.01); *H04N 23/56* (2023.01); *G06V 40/1312* (2022.01); *G06V 40/1341* (2022.01); *G06V 40/14* (2022.01)

(56) References Cited

U.S. PATENT DOCUMENTS

| | | | | |
|---|---|---|---|---|
| 9,971,948 | B1* | 5/2018 | Herrington | G06V 40/10 |
| 2008/0008365 | A1 | 1/2008 | Hikita et al. | |
| 2013/0329031 | A1* | 12/2013 | Miura | G06V 40/145 348/77 |
| 2015/0363986 | A1 | 12/2015 | Hoyos et al. | |
| 2016/0358332 | A1 | 12/2016 | Watanabe | |
| 2016/0373669 | A1* | 12/2016 | Ando | H04N 5/332 |
| 2017/0366726 | A1* | 12/2017 | Yanagida | H04N 5/2353 |
| 2018/0176496 | A1* | 6/2018 | Nakamura | A61B 5/0042 |
| 2020/0125832 | A1* | 4/2020 | Zhang | G06T 7/557 |
| 2020/0297222 | A1* | 9/2020 | Shiono | G01N 21/272 |
| 2020/0410200 | A1* | 12/2020 | Davis | G06V 40/1318 |
| 2021/0012092 | A1* | 1/2021 | Purves | G06V 10/141 |
| 2021/0085229 | A1* | 3/2021 | Narumi | A61B 5/0261 |
| 2021/0259565 | A1* | 8/2021 | Ohno | H04N 5/374 |
| 2022/0400224 | A1* | 12/2022 | Wang | H04N 5/23245 |

FOREIGN PATENT DOCUMENTS

| | | |
|---|---|---|
| JP | 2005-312887 | 11/2005 |
| JP | 2008-020942 | 1/2008 |
| JP | 2010-522379 A | 7/2010 |
| JP | 2017-091186 | 5/2017 |
| WO | WO2008134135 A2 | 11/2008 |

OTHER PUBLICATIONS

Shree K. Nayar et al., "Fast Separation of Direct and Global Components of a Scene using High Frequency Illumination", SIGGRAPH Conference Boston, Jul. 2006.

Non-Final Office Action dated Apr. 26, 2024 issued in U.S. Appl. No. 18/486,821.

English Translation of Chinese Search Report dated Nov. 20, 2023 for the related Chinese Patent Application No. 201980022548.7.

* cited by examiner

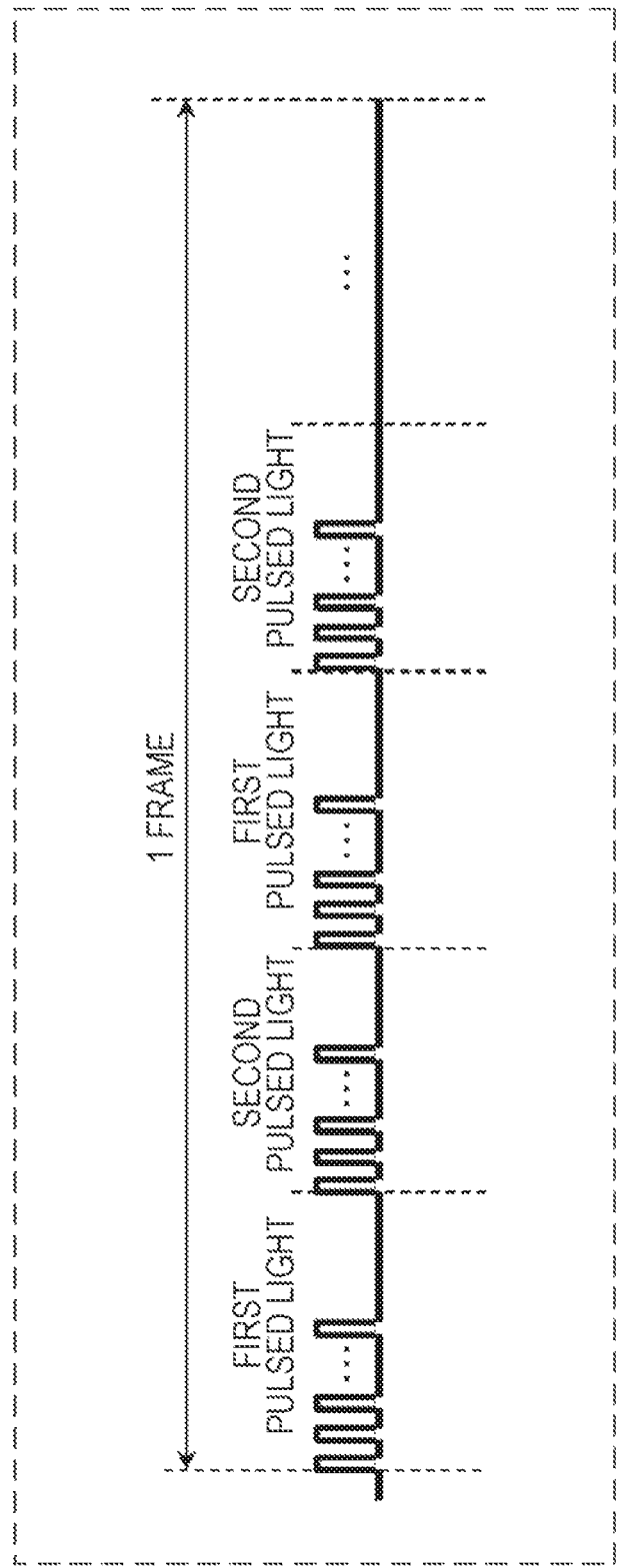

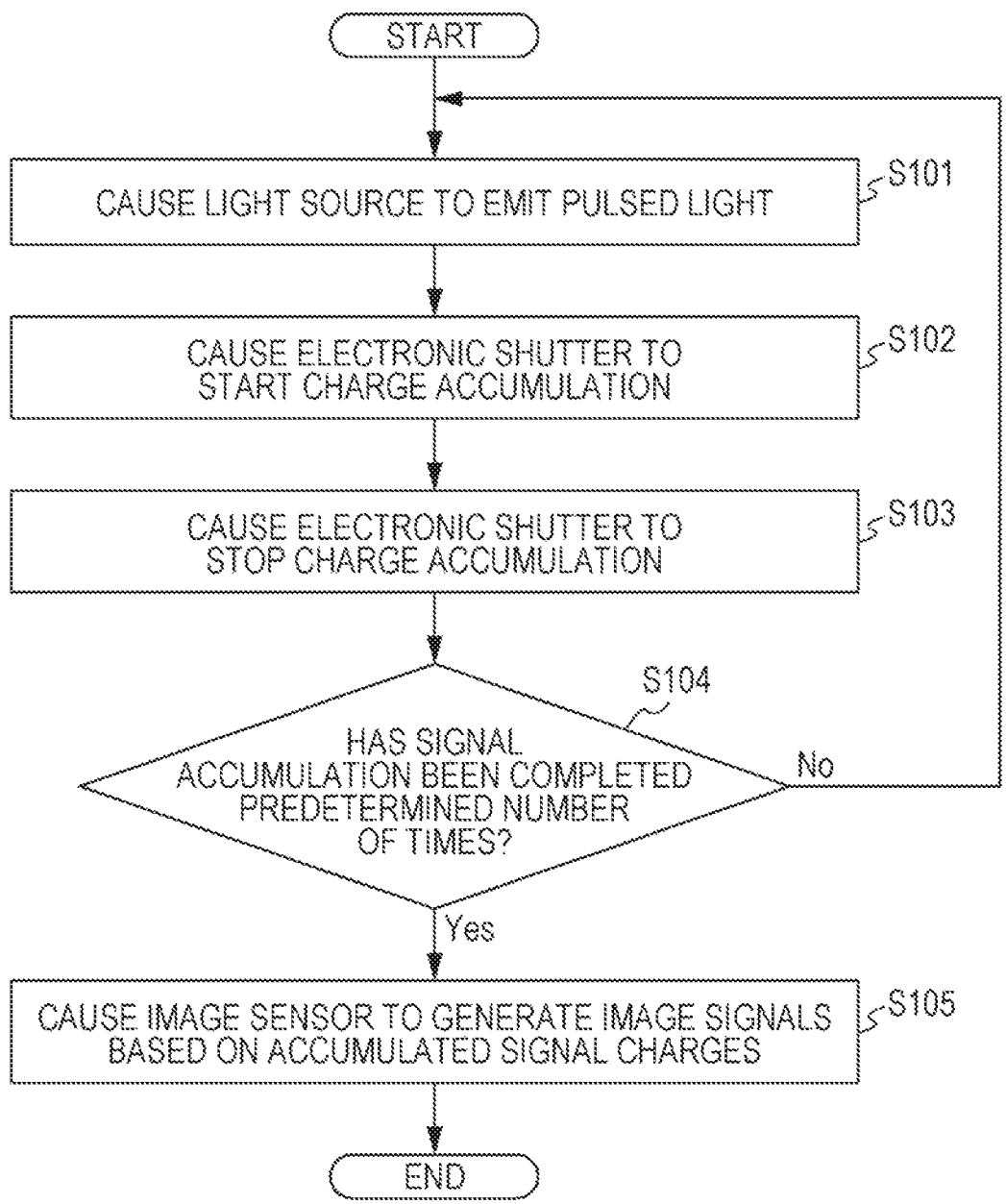

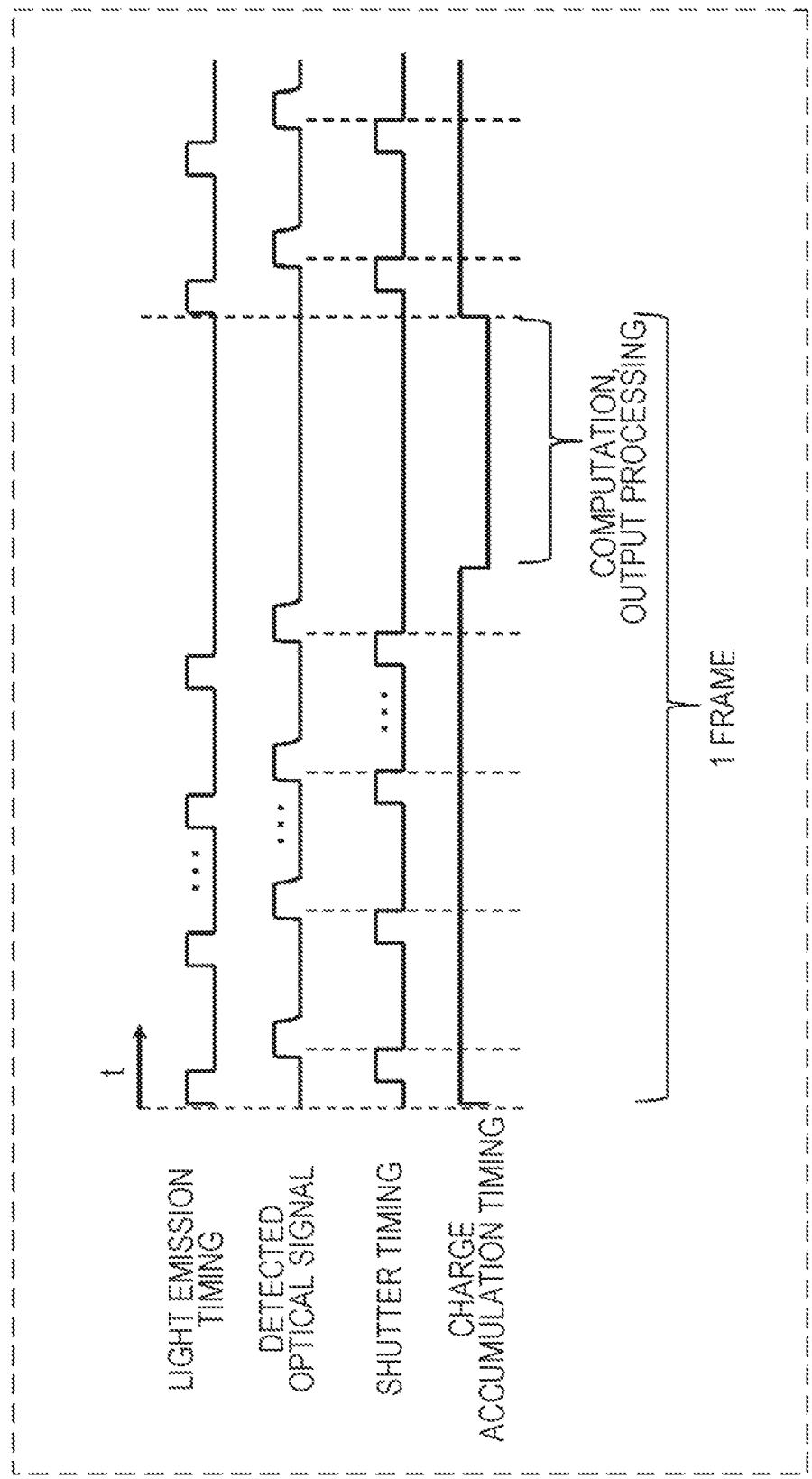

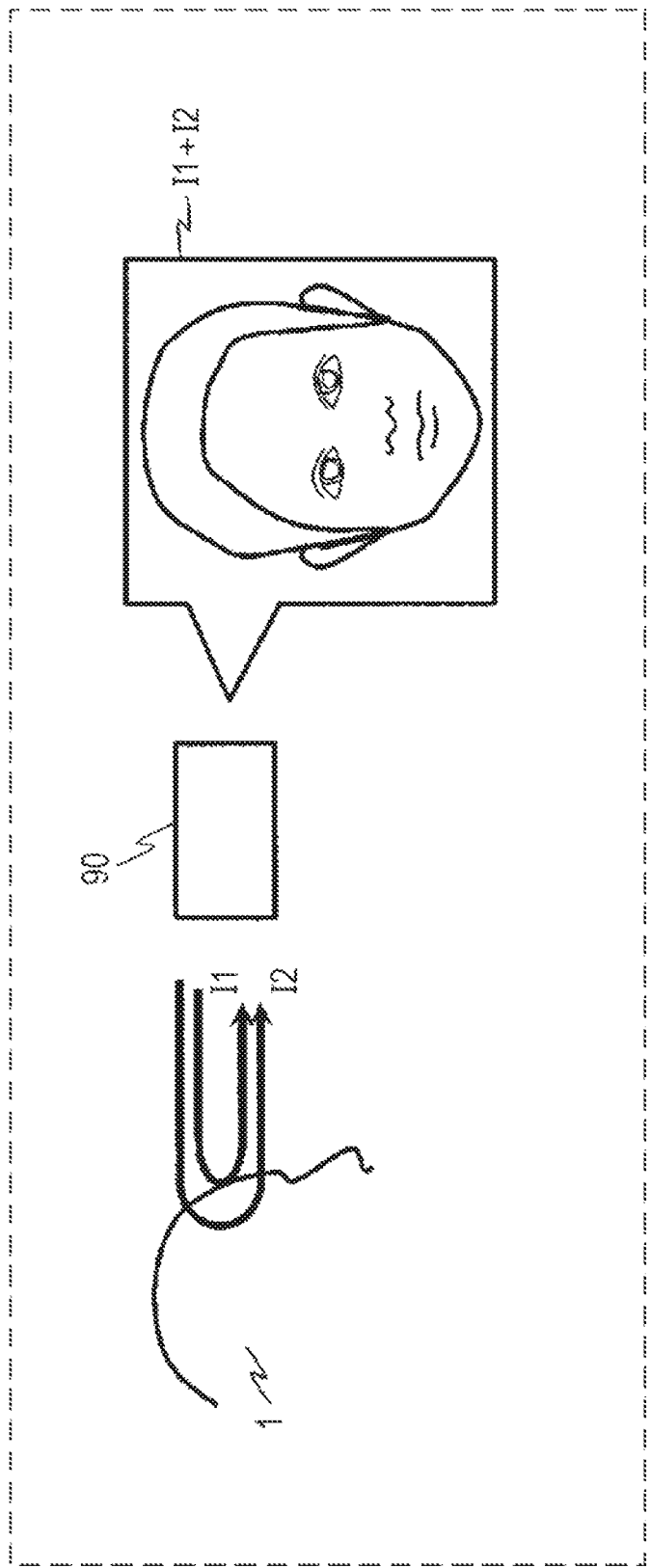

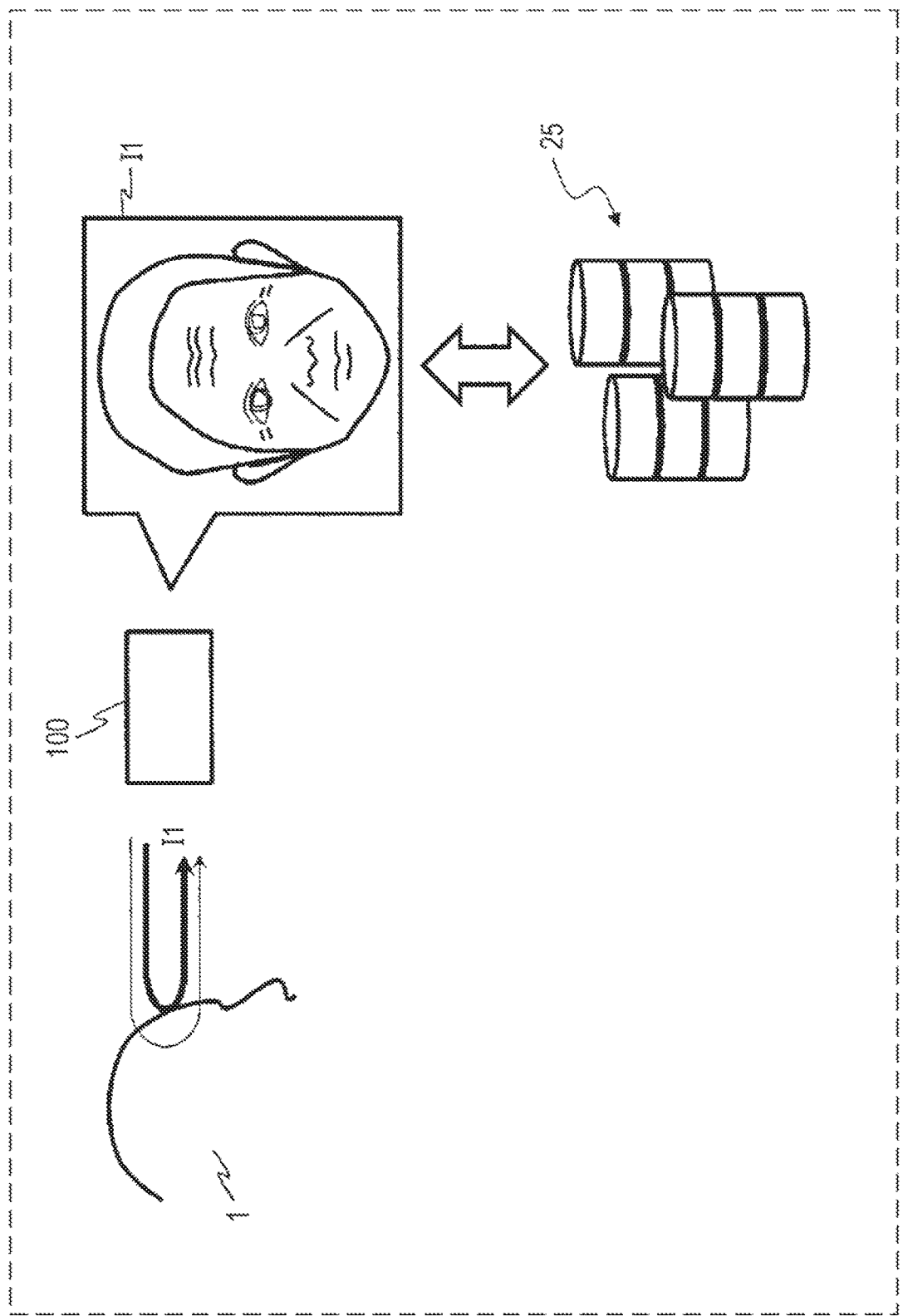

IDENTIFYING DEVICE AND IDENTIFYING METHOD USING REFLECTED LIGHT FROM A BODY OF A USER IRRADIATED BY PULSED LIGHT

BACKGROUND

1. Technical Field

The present disclosure relates to an identifying device and an identifying method.

2. Description of the Related Art

In the field of individual identification, the authentication is in transition from password authentication to biometric authentication. In password authentication, the authentication is performed based on a password entered by a user. In biometric authentication, on the other hand, the authentication is performed based on information regarding a physical feature of the human. Biometric authentication also has an advantage in that the risks of forgetting, leakage, and brute-force attacks are low. In biometric authentication, for example, a portion of the body of a user is illuminated with light, and reflected light is observed to thereby obtain information for individual identification.

Japanese Unexamined Patent Application Publication No. 2008-020942 discloses a method for enhancing the accuracy of biometric authentication of a user. In the method disclosed in Japanese Unexamined Patent Application Publication No. 2008-020942, fingerprint-based authentication and vein-based authentication are combined together to perform biometric authentication of a user. More specifically, the surface of a user's finger is illuminated with a light having a wavelength of 900 nm for fingerprint-based authentication and light having a wavelength of 750 nm for vein-based authentication. Based on reflected light of the light having those wavelengths, the user is authenticated.

SUMMARY

In one general aspect, the techniques disclosed here feature an identifying device including: a light source; an image sensor; a memory that stores biometric data indicating a feature of a body of a user; and a processor. The processor causes the light source to emit pulsed light having a pulse duration of more than or equal to 0.2 ns and less than or equal to 1 µs to illuminate the user with the pulsed light, causes the image sensor to detect at least part of reflected pulsed light that returns from the user and to output a signal corresponding to two-dimensional distribution of an intensity of the at least part of the reflected pulsed light, and verifies the signal against the biometric data to identify the user.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1F is a diagram illustrating one example of an operation in one frame;

FIG. 1G is a flowchart illustrating an overview of operations performed by a control circuit;

FIG. 3A is one example of a timing chart when surface reflection components are detected;

FIG. 5A is a diagram schematically illustrating a state in which a user is photographed with an ordinary camera;

FIG. 5B is a diagram schematically illustrating one example of photography of the user by using the surface reflection components in the present embodiment;

DETAILED DESCRIPTION

The embodiment described below represents a general or specific example. Numerical values, shapes, materials, constituent elements, the arrangement positions of the constituent elements, and so on described in the embodiment are examples and are not intended to limit the present disclosure. Also, of the constituent elements in the embodiment described below, the constituent elements not set forth in the independent claims that represent the broadest concept will be described as optional constituent elements.

In the present disclosure, all or a part of circuits, units, devices, parts, or portions or all or a part of functional blocks in the block diagrams can be implemented as one or more electronic circuits including, but not limited to, a semiconductor device, a semiconductor integrated circuit (IC), or a large-scale integration (LSI). The LSI or IC can be integrated into one chip or also can be a combination of a plurality of chips. For example, functional blocks other than a storage device may be integrated into one chip. Although the name used here is an LSI or IC, it may also be called a system LSI, a very large-scale integration (VLSI), or an ultra large-scale integration (ULSI) depending on the degree of integration. A field programmable gate array (FPGA) that can be programmed after manufacturing an LSI or a reconfigurable logic device that allows reconfiguration of the connection relationship inside the LSI or setup of circuit cells inside the LSI can also be used for the same purpose.

In addition, the functions or operations of all or a part of the circuits, units, devices, parts, or portions can be implemented by executing software. In such a case, the software is recorded on one or more non-transitory recording media, such as a read-only memory (ROM), an optical disk, or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices such as an interface.

An embodiment will be described in detail below with reference to the accompanying drawings.

Embodiment

[1. Identifying Device]

First, the configuration of an identifying device 100 in an embodiment of the present disclosure will be described with reference to FIGS. 1A to 1G.

Figure 1A:
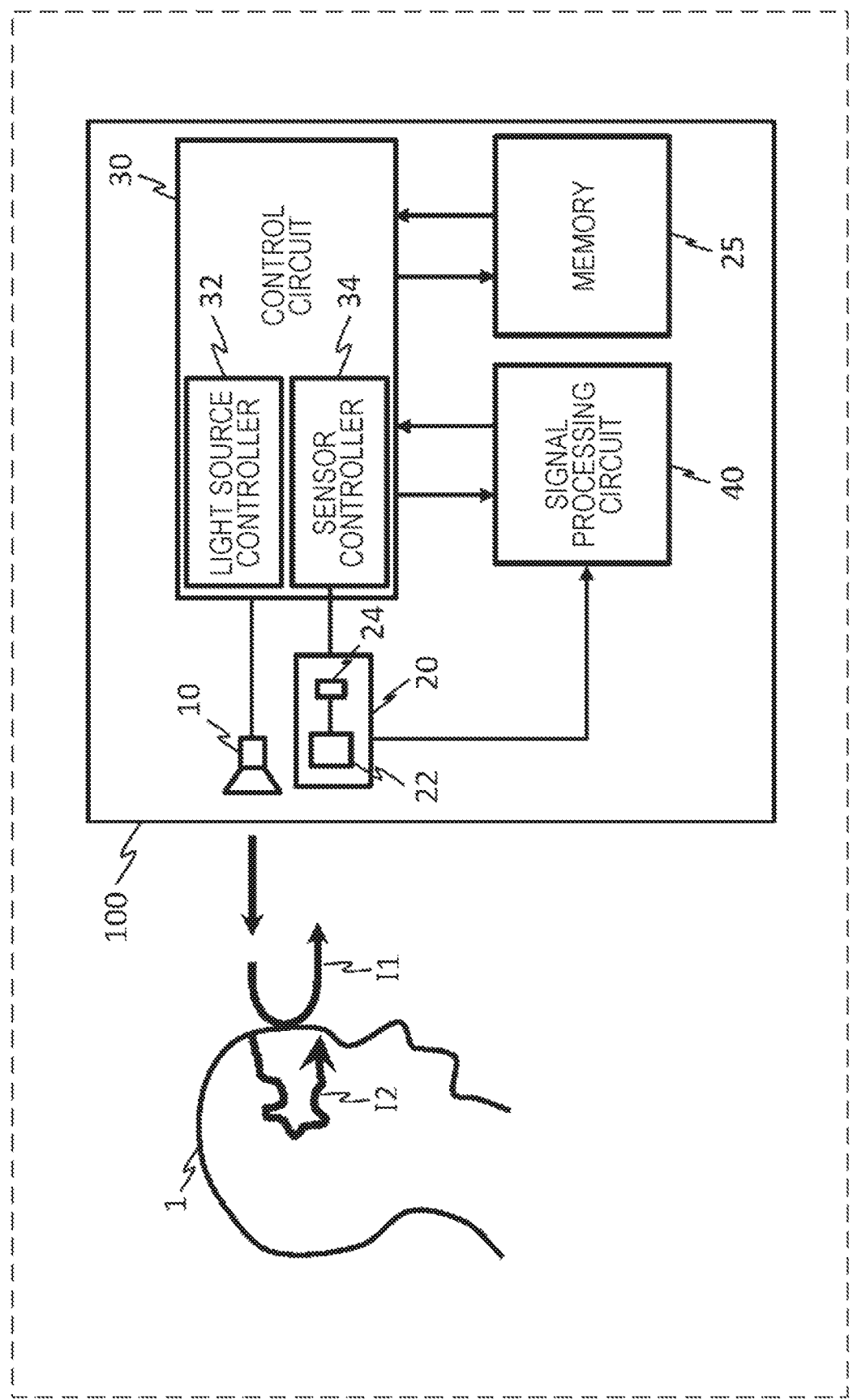
FIG. 1A is a diagram schematically illustrating one example of an identifying device in an embodiment of the present disclosure.

FIG. 1A is a diagram schematically illustrating one example of the identifying device 100 in the present embodiment. The identifying device 100 includes a light source 10, an image sensor 20, a memory 25, a control circuit 30, and a signal processing circuit 40. The image sensor 20 includes a plurality of photoelectric conversion elements 22 and a plurality of charge accumulation portions 24. Herein, the control circuit 30 and the signal processing circuit 40 may be collectively referred to as a "processor".

The light source 10 emits pulsed light with which the head portion of a user 1 is illuminated. The image sensor 20 detects at least part of pulsed light that returns from the head portion of the user 1. The control circuit 30 controls the light source 10 and the image sensor 20. The signal processing circuit 40 processes signals output from the image sensor 20.

In the present embodiment, the control circuit 30 includes a light source controller 32 that controls the light source 10 and a sensor controller 34 that controls the image sensor 20. The light source controller 32 controls the intensity, the pulse duration, the emission timing, and/or the wavelength of the pulsed light emitted from the light source 10. The sensor controller 34 controls the timing of signal accumulation in each pixel in the image sensor 20.

The individual constituent elements will be described below in more detail.

[1-1. Light Source 10]

The light source 10 illuminates the head portion, for example, the forehead, of the user 1 with light. The light that is emitted from the light source 10 and that reaches the user 1 splits into surface reflection components I1 that are reflected by a surface of the user 1 and internal scatter components I2 that are scattered inside the user 1. The internal scatter components I2 are components that are reflected or scattered once or components that are scattered multiple times inside the living body. When the forehead of the user 1 is illuminated with light, the internal scatter components I2 refer to components that reach a portion, for example, the brain, at a depth of about 8 to 16 mm from the surface of the forehead and that return to the identifying device 100 again. The surface reflection components I1 include three components: a direct reflection component, a diffusion reflection component, and a scatter reflection component. The direct reflection component is a reflection component whose incident angle and reflection angle are equal to each other. The diffusion reflection component is a component that is diffused and reflected by an uneven shape on a surface. The scatter reflection component is a component that is scattered and reflected by internal tissue in the vicinity of a surface. When the forehead of the user 1 is illuminated with light, the scatter reflection component is a component that is scattered and reflected inside the epidermis. Hereinafter, in the present disclosure, the surface reflection components I1 that are reflected by the surface of the user 1 are assumed to include those three components. The surface reflection components I1 and the internal scatter components I2 change in traveling direction owing to reflection or diffusion, and some of the surface reflection components I1 and the internal scatter components I2 reach the image sensor 20.

In accordance with an instruction from the control circuit 30, the light source 10 repeatedly generates pulsed light a plurality of times at predetermined time intervals or at a predetermined timing. The pulsed light generated by the light source 10 can have, for example, a rectangular wave whose falling period is nearly zero. The falling period is a period from when the intensity of the pulsed light starts decreasing until the decrease ends. Components of the pulsed light in the falling period thereof are referred to as a trailing edge of the pulsed light. In general, light that is incident on the user 1 propagates in the user 1 through various paths and is emitted from the surface of the user 1 with time differences. Thus, the trailing edge of the internal scatter components I2 of the pulsed light has a spread. When the target portion is the forehead, the spread of the trailing edge of the internal scatter components I2 is about 4 ns. When this is considered, the falling period of the pulsed light can be set to, for example, 2 ns or less, which is half or less of the spread. The falling period may be 1 ns or less, which is further half of that falling period. On the other hand, components of the pulsed light in the rising period thereof can be used to detect the surface reflection components I1. The rising period is a period from when the intensity of the pulsed light starts increasing until the increase ends. Components of the pulsed light in the rising period thereof are also referred to as a "leading edge of the pulsed light".

The light source 10 may be configured by combining a light source, such as a laser, and a diffuser plate. The laser is, for example, a laser diode (LD). Use of a laser allows for light outputting with high temporal responsiveness. Light outputting with high temporal responsiveness has a waveform with a steep rising characteristic or falling characteristic. The rising characteristic and the falling characteristic are also referred to as a "Tr characteristic" and a "Tf characteristic", respectively. When a diffuser plate is disposed in front of the light source 10, the user 1 can be two-dimensionally illuminated with the light.

The light emitted by the light source 10 may have an arbitrary wavelength included in a wavelength range of, for example, 650 to 950 nm. This wavelength range is included a wavelength range of red to near-infrared. Herein, terms for "light" are used not only for visible light but also for infrared. The aforementioned wavelength range is called the "biological window" and has a characteristic of being relatively less likely to be absorbed by the in-vivo water and the skin. When the detection target is a living body, use of light in the aforementioned wavelength range can increase the detection sensitivity.

In the identifying device 100 in the present embodiment, the light source 10 that is designed considering influences on the retina can be used in order to perform measurement on the user 1 in a contactless manner. For example, the light source 10 that satisfies class 1 of a laser safety standard formulated in each country can be used. When class 1 is satisfied, the user 1 is illuminated with low-illuminance light with which the accessible emission level (AEL) falls below 1 mW. The light source 10 itself does not necessarily have to satisfy class 1. For example, a diffuser plate, a neutral density (ND) filter, or the like may be disposed in front of the light source 10 to diffuse or attenuate light to satisfy class 1 of the laser safety standard.

Heretofore, streak cameras have been used in order to perform detection through discrimination of information, such as absorption coefficients or diffusion coefficients, at different places in a depth direction inside a living body. For example, one example of such streak cameras is disclosed in Japanese Unexamined Patent Application Publication No. 4-189349. In those streak cameras, ultrashort pulsed light having a pulse duration of femtoseconds or picoseconds has been used in order to perform measurement with desired spatial resolutions. The "pulse duration" as used herein refers to a full duration at half maximum of a pulse. As opposed to a method using a conventional streak camera, the identifying device 100 in the present embodiment can discriminate and detect the surface reflection components I1 and the internal scatter components I2. Accordingly, the pulsed light emitted by the light source 10 does not necessarily have to be ultrashort pulsed light, and the pulse duration of the pulsed light can be arbitrarily selected.

For illuminating the forehead with light, the amount of light of the internal scatter components I2 can have a very small value, which is about one several-thousandths to one several-tenths of thousands of the amount of light of the surface reflection components I1. In addition, when the safety standards of the laser are considered, the amount of light that can be emitted is significantly small, thus making it very difficult to detect the internal scatter components I2. Even in this case, when the light source 10 generates pulsed light having a relatively long pulse duration, it is possible to increase the amount of summation of the internal scatter components I2 which involves a time delay. This can increase the amount of light that is detected and can enhance the signal-to-noise (S/N) ratio.

Figure 1B:
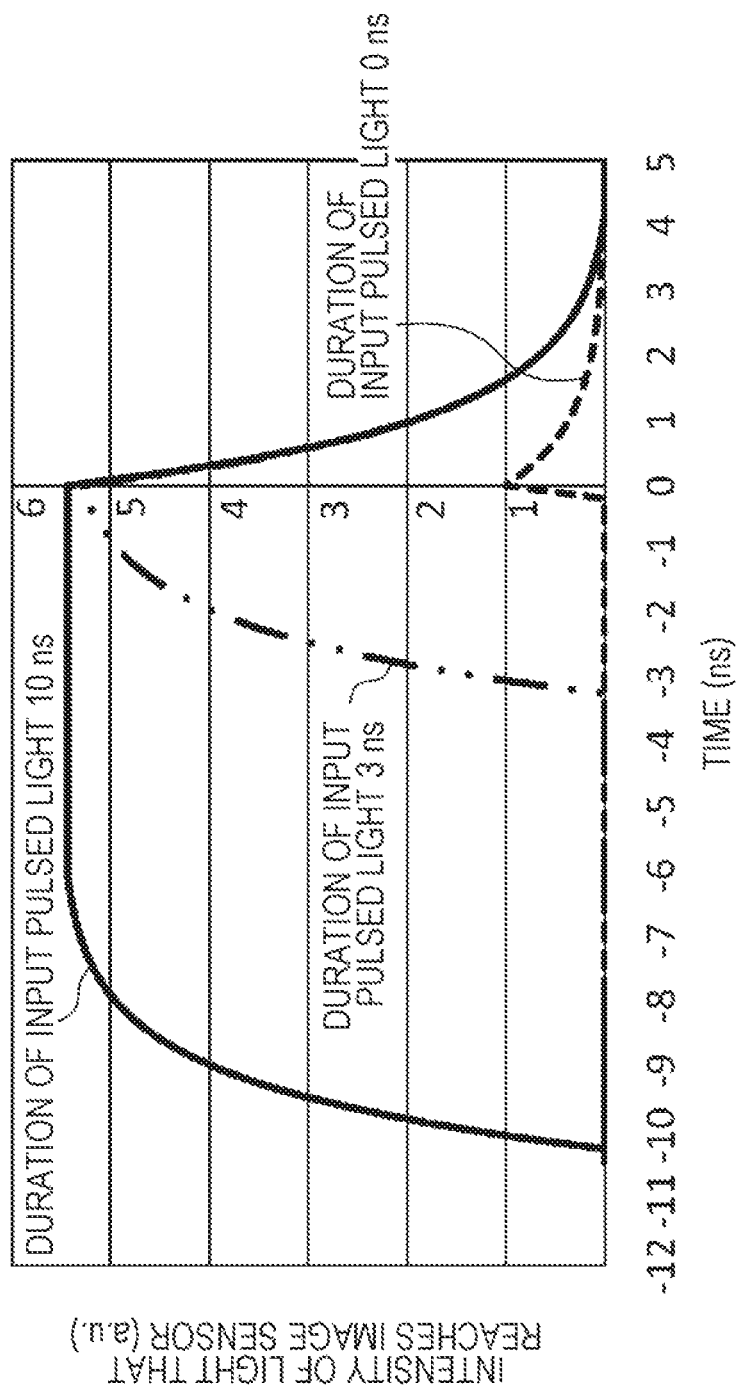
FIG. 1B is a graph illustrating one example of changes over time in intensities of light that reaches an image sensor.
Figure 1C:
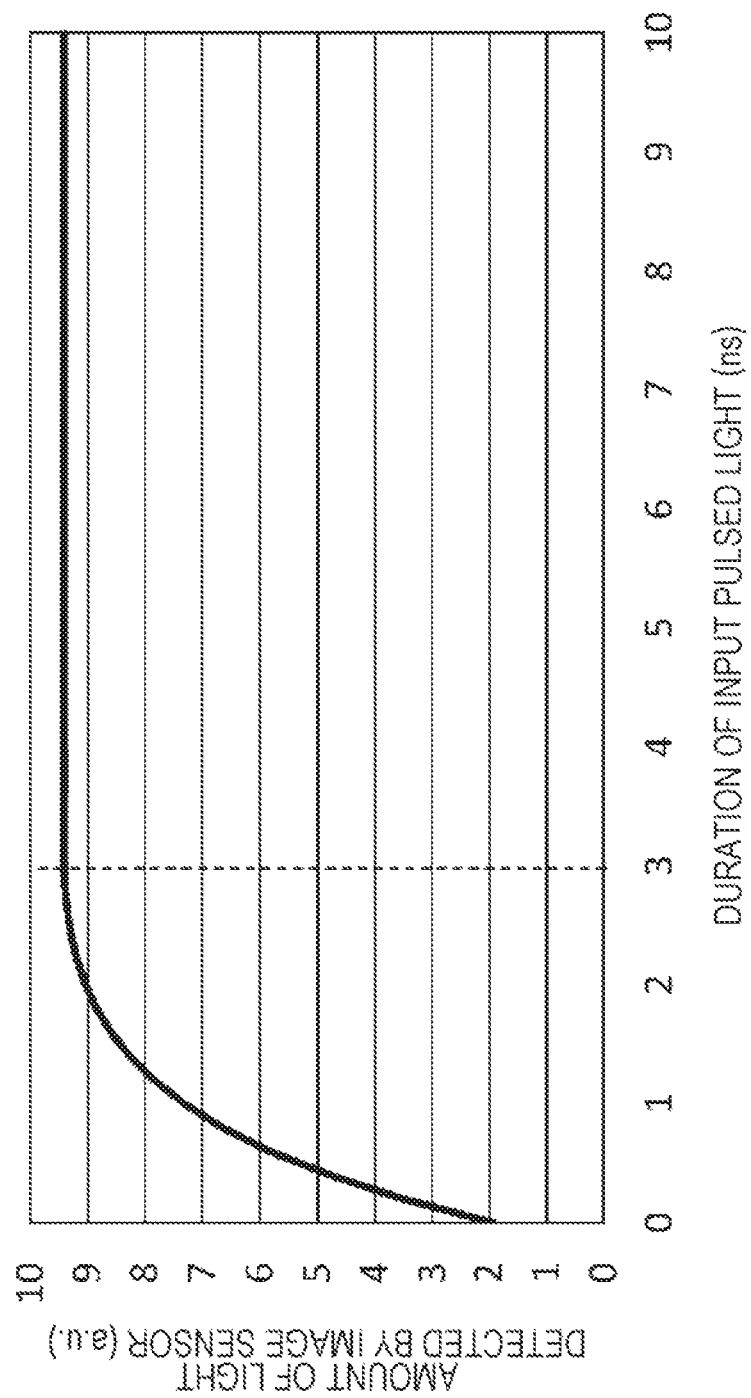
FIG. 1C is a graph in which the horizontal axis represents the duration of input pulsed light, and the vertical axis represents the amount of light detected by the image sensor.

The light source 10 emits, for example, pulsed light having a pulse duration of 3 ns or more. In general, the temporal spread of light that is scattered in physiological tissues, such as the brain, is about 4 ns. FIG. 1B illustrates an example of changes over time in the amounts of light that reaches the image sensor 20 in respective cases in which the durations of input pulsed light are 0 ns, 3 ns, and 10 ns. As illustrated in FIG. 1B, as the duration of the pulsed light from the light source 10 is increased, the amount of light of the internal scatter components I2 that appear at the trailing edge of pulsed light that returns from the user 1 increases. FIG. 1C is a graph in which the horizontal axis represents the duration of input pulsed light, and the vertical axis represents the amount of light detected by the image sensor 20. The image sensor 20 has an electronic shutter. The result in FIG. 1C was obtained under a condition that the electronic shutter was opened when 1 ns passed after the time point at which the trailing edge of the pulsed light reflected by the surface of the user 1 reached the image sensor 20. The reason why this condition was selected is that immediately after the trailing edge of the pulsed light reaches the image sensor 20, the ratio of the surface reflection components I1 to the internal scatter components I2 is high. As illustrated in FIG. 1C, when the pulse duration of the pulsed light emitted by the light source 10 is set to 3 ns or more, it is possible to maximize the amount of light detected by the image sensor 20.

Also, the resolution of timing control performed by a drive circuit for the light source 10 and the electronic shutter is about 0.2 ns. Thus, the pulse duration of the light source 10 is set to, for example, 0.2 ns or more.

The light source 10 may emit pulsed light having a pulse duration of 5 ns or more or further 10 ns or more. On the other hand, when the pulse duration is too long, the amount of light that is not used increases and is thus wasteful. Hence, the light source 10 generates, for example, pulsed light having a pulse duration of 50 ns or less. Alternatively, the light source 10 may emit pulsed light having a pulse duration of 30 ns or less or further 20 ns or less.

The illumination pattern of the light source 10 may be, for example, a pattern having uniform-intensity distribution in an illumination area. This is due to the following reason. In the identifying device 100 in the present embodiment, the surface reflection components I1 are temporally separated and reduced. Thus, the internal scatter components I2 can also be detected at a null point that is directly below an illumination point on the user 1. Accordingly, the identifying device 100 in the present embodiment can enhance the measurement resolution by illuminating a spatially wide range of a target portion of the user 1.

[1-2. Image Sensor 20]

The image sensor 20 receives light that is emitted from the light source 10 and that is reflected or scattered by the user 1. The image sensor 20 has a plurality of two-dimensionally arranged light-detecting cells to obtain two-dimensional information of the user 1 at a time. This allows the two-dimensional information of the user 1 to be obtained in a relatively short period of time, compared with a line sensor that performs detection while sliding a target portion of the user 1. Herein, the light-detecting cells may be referred to as "pixels". The image sensor 20 is, for example, an arbitrary imaging device, such as a charge-coupled device (CCD) image sensor or a complementary metal-oxide semiconductor (CMOS) image sensor.

The electronic shutter for the image sensor 20 is a circuit for controlling an imaging timing. In the present embodiment, the sensor controller 34 in the control circuit 30 has functions of the electronic shutter. The electronic shutter controls a single-signal-accumulation period in which received light is converted into effective electrical signals and the electrical signals are stored and a period in which the signal accumulation is stopped. The signal accumulation period can also be referred to as an "exposure period". The length of the exposure period may be referred to as a "shutter duration" in the description below. The time from when one exposure period ends until a next exposure period starts may be referred to as a "non-exposure period". Hereinafter, a state in which exposure is performed may be referred to as "open", and a state in which exposure is stopped may be referred to as "close".

The image sensor 20 can adjust the exposure period and the non-exposure period in the range of subnanoseconds, for example, in the range of 30 ps to 1 ns, by using the electronic shutter. In order to correct influences of the brightness of a subject, conventional time-of-flight (ToF) cameras intended for distance measurement detect all light that returns via reflection by the subject after being emitted from the light source 10. Accordingly, in the conventional ToF cameras, the shutter duration needs to be longer than the pulse duration of light. In contrast, in the identifying device 100 in the present embodiment, it is not necessary to correct the amount of light from a subject. Thus, the shutter duration does not need to be longer than the pulse duration. Hence, the shutter duration can be set to, for example, a value of 1 to 30 ns. According to the identifying device 100 in the present embodiment, since the shutter duration can be reduced, it is possible to reduce influences of dark current included in detection signals.

For illuminating the forehead of the user 1 with light, the decay rate of light inside the forehead is very large. For example, the emitted light can decay to about one millionth of the incident light. Thus, there are cases in which the amount of light is not sufficient with only illumination of a single pulse in order to detect the internal scatter components I2. The amount of light is particularly very small with illumination at class 1 of the laser safety standard. In this case, the light source 10 emits the pulsed light a plurality of times, and correspondingly, the image sensor 20 also performs exposure a plurality of times by using the electronic shutter, to thereby make it possible to improve the sensitivity through summation of detection signals.

A configuration example of the image sensor 20 will be described below.

The image sensor 20 includes a plurality of pixels that is two-dimensionally arrayed on an imaging plane. Each pixel can include, for example, a photoelectric conversion element, such as a photodiode, and one or more charge accumulation portions. The description below will be given of an example in which each pixel includes a photoelectric conversion element that performs photoelectric conversion to generate signal charge corresponding to the amount of received light, a charge accumulation portion that accumulates signal charge generated based on the surface reflection components I1 of the pulsed light, and a charge accumulation portion that accumulates signal charge generated based on the internal scatter components I2 of the pulsed light. In an example below, the control circuit 30 causes the image sensor 20 to detect pre-falling-start part of pulsed light that returns from the head portion of the user 1, to thereby detect the surface reflection components I1. The control circuit 30 also causes the image sensor 20 to detect post-falling-start part of the pulsed light that returns from the head portion of the user 1, to thereby detect the internal scatter components I2. The light source 10 emits, for example, light with two types of wavelength.

Figure 1D:
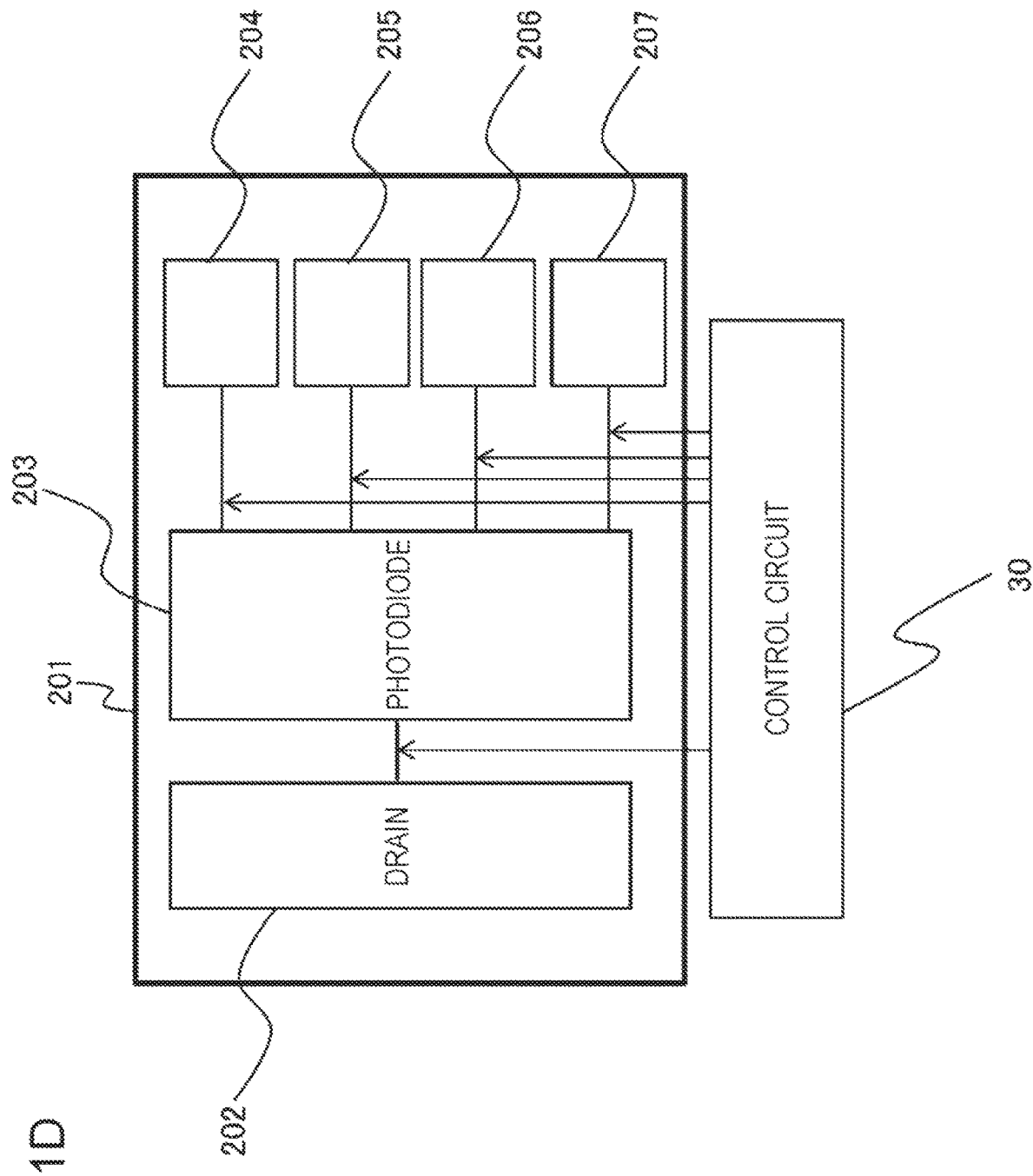
FIG. 1D is a diagram illustrating one example of a schematic configuration of one pixel in the image sensor.

FIG. 1D is a diagram illustrating one example of a schematic configuration of one pixel 201 in the image sensor 20. FIG. 1D schematically illustrates the configuration of one pixel 201 and does not necessarily reflect the actual structure thereof. The pixel 201 in this example includes a photodiode 203 that performs photoelectric conversion, a first floating diffusion layer 204, a second floating diffusion layer 205, a third floating diffusion layer 206, and a fourth floating diffusion layer 207, which are charge accumulation portions, and a drain 202 that discharges signal charge.

The photodiode 203 converts photons that are incident on each pixel as a result of a single emission of pulsed light into signal electrons, which are signal charge. The converted signal electrons are discharged to the drain 202 in accordance with a control signal input from the control circuit 30 or are sorted to any of the first floating diffusion layer 204, the second floating diffusion layer 205, the third floating diffusion layer 206, and the fourth floating diffusion layer 207.

The emission of the pulsed light from the light source 10, the accumulation of signal charges in the first floating diffusion layer 204, the second floating diffusion layer 205, the third floating diffusion layer 206, and the fourth floating diffusion layer 207, and the discharge of the signal charge to the drain 202 are repeatedly performed in that order. This repetition operation is performed at high speed and can be repeated, for example, tens of thousands of times to hundreds of millions of times within the time of one frame. The time of one frame is, for example, about 1/30 second. Eventually, the pixel 201 generates four image signals based on the signal charges accumulated in the first floating diffusion layer 204, the second floating diffusion layer 205, the third floating diffusion layer 206, and the fourth floating diffusion layer 207 and outputs the four image signals.

The control circuit 30 in this example causes the light source 10 to sequentially and repeatedly emit first pulsed light having a first wavelength and second pulsed light having a second wavelength. Selecting two wavelengths having different absorption rates for the internal tissues of the user 1 as the first wavelength and the second wavelength makes it possible to analyze the state of the user 1.

The control circuit 30 first causes the light source 10 to emit the first pulsed light. In a first period in which the surface reflection components I1 of the first pulsed light are incident on the photodiode 203, the control circuit 30 causes signal charge to be accumulated in the first floating diffusion layer 204. Subsequently, in a second period in which the internal scatter components I2 of the first pulsed light are incident on the photodiode 203, the control circuit 30 causes signal charge to be accumulated in the second floating diffusion layer 205. In a third period in which the surface reflection components I1 of the second pulsed light are incident on the photodiode 203, the control circuit 30 causes signal charge to be accumulated in the third floating diffusion layer 206. Subsequently, in a fourth period in which the internal scatter components I2 of the second pulsed light are incident on the photodiode 203, the control circuit 30 causes signal charge to be accumulated in the fourth floating diffusion layer 207.

As described above, after starting emission of the first pulsed light, the control circuit 30 causes signal charge from the photodiode 203 to be sequentially accumulated in the first floating diffusion layer 204 and the second floating diffusion layer 205 with a predetermined time difference therebetween. Thereafter, after starting emission of the second pulsed light, the control circuit 30 causes signal charge from the photodiode 203 to be sequentially accumulated in the third floating diffusion layer 206 and the fourth floating diffusion layer 207 with a predetermined time difference therebetween. The above-described operation is repeated a plurality of times. A period in which signal charge is accumulated in another floating diffusion layer (not illustrated) when the light source 10 is turned off may be provided in order to estimate the amount of light of external light and ambient light. By subtracting the amount of the signal charge in the aforementioned other floating diffusion layer from the amount of signal charges accumulated in the first floating diffusion layer 204, the second floating diffusion layer 205, the third floating diffusion layer 206, and the fourth floating diffusion layer 207, it is possible to obtain signals from which components of external light and ambient light are eliminated.

Although the number of charge accumulation portions per pixel is four in the present embodiment, the number may be designed to an arbitrary number that is one or more, depending on the purpose. For example, when only one type of wavelength is used, the number of charge accumulation portions may be two. Also, for an application in which the number of types of wavelength to be used is one, and only the surface reflection components I1 or only the internal scatter components I2 are detected, the number of charge accumulation portions per pixel may be one. Also, even for an application in which two or more types of wavelength are used, the number of charge accumulation portions may be one when imaging using one of the wavelengths and imaging using another wavelength are performed in respective different frames. Also, when the detection of the surface reflection components I1 and the detection of the internal scatter components I2 are performed in respective different frames, as described below, the number of charge accumulation portions may be one.

Figure 1E:
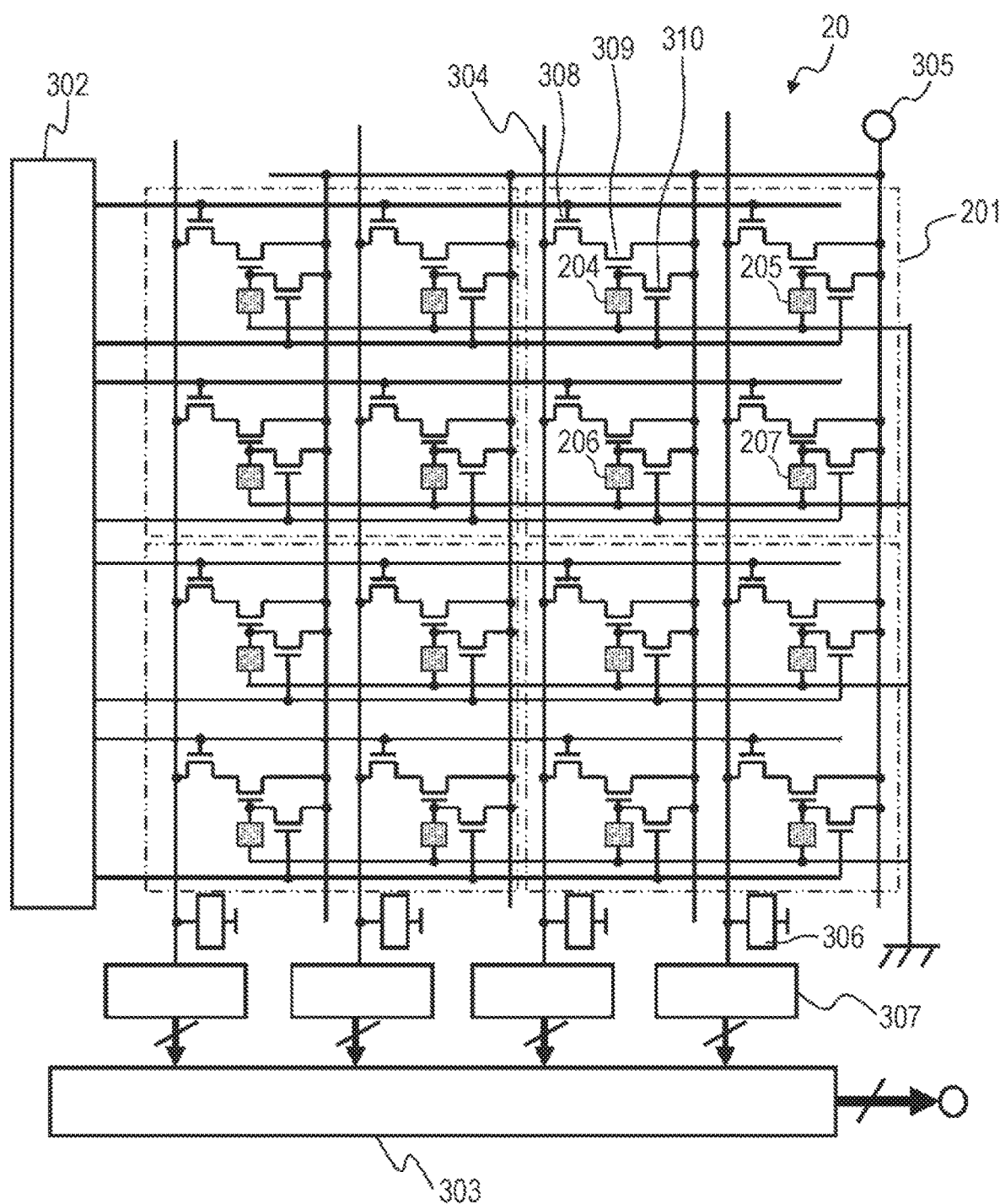
FIG. 1E is a diagram illustrating one example of the configuration of the image sensor.

FIG. 1E is a diagram illustrating one example of the configuration of the image sensor 20. In FIG. 1E, each area surrounded by a chain double-dashed line frame corresponds to one pixel 201. Each pixel 201 includes one photodiode. Although FIG. 1E illustrates only four pixels arrayed in two rows and two columns, a larger number of pixels can be arranged in practice. Each pixel 201 includes the first floating diffusion layer 204, the second floating diffusion layer 205, the third floating diffusion layer 206, and the fourth floating diffusion layer 207. The signals accumulated in the first floating diffusion layer 204, the second floating diffusion layer 205, the third floating diffusion layer 206, and the fourth floating diffusion layer 207 are treated as if they were signals of four pixels in a typical CMOS image sensor and are output from the image sensor 20.

Each pixel 201 has four signal detection circuits. Each signal detection circuit includes a source follower transistor 309, a row selecting transistor 308, and a reset transistor 310. In this example, the reset transistor 310 corresponds to the drain 202 illustrated in FIG. 1D, and a pulse that is input to a gate of the reset transistor 310 corresponds to a drain discharge pulse. Although each transistor is, for example, a field-effect transistor formed at a semiconductor substrate, the transistor is not limited thereto. As illustrated in FIG. 1E, one of an input terminal and an output terminal of the source follower transistor 309 and one of an input terminal and an output terminal of the row selecting transistor 308 are connected to each other. One of the input terminal and the output terminal of the source follower transistor 309 is typically a source. One of the input terminal and the output terminal of the row selecting transistor 308 is typically a drain. A gate that is a control terminal of the source follower transistor 309 is connected to the photodiode 203. Signal charge generated by the photodiode 203 is accumulated in a floating diffusion layer, which is a charge accumulation portion between the photodiode 203 and the source follower transistor 309. The signal charge consists of holes or electrons.

Although not illustrated in FIG. 1E, the first floating diffusion layer 204, the second floating diffusion layer 205, the third floating diffusion layer 206, and the fourth floating diffusion layer 207 are connected to the photodiode 203. A switch can be provided between the photodiode 203 and the first floating diffusion layer 204, the second floating diffusion layer 205, the third floating diffusion layer 206, and the fourth floating diffusion layer 207. In accordance with a signal accumulation pulse from the control circuit 30, the switch switches a conductive state between the photodiode 203 and each of the first floating diffusion layer 204, the second floating diffusion layer 205, the third floating diffusion layer 206, and the fourth floating diffusion layer 207. This controls the start and stop of accumulation of signal charge in each of the first floating diffusion layer 204, the second floating diffusion layer 205, the third floating diffusion layer 206, and the fourth floating diffusion layer 207. The electronic shutter in the present embodiment has a mechanism for such exposure control.

The signal charges accumulated in the first floating diffusion layer 204, the second floating diffusion layer 205, the third floating diffusion layer 206, and the fourth floating diffusion layer 207 are read when a row selecting circuit 302 turns on a gate of the row selecting transistor 308. During the reading, current that flows from a source follower power source 305 into the source follower transistor 309 and a source follower load 306 is amplified in accordance with signal potentials in the first floating diffusion layer 204, the second floating diffusion layer 205, the third floating diffusion layer 206, and the fourth floating diffusion layer 207. Analog-to-digital (AD) conversion circuits 307 connected to respective columns convert analog signals due to the current, read from vertical signal lines 304, into digital signal data. A column selecting circuit 303 reads the digital signal data for each column, and the digital signal data is output from the image sensor 20. After performing reading from one row, the row selecting circuit 302 and the column selecting circuit 303 perform reading from a next row, and thereafter, reading of information of signal charges in the floating diffusion layers in all rows is similarly performed. After reading all the signal charges, the control circuit 30 turns on the gates of the reset transistors 310 to thereby reset all the floating diffusion layers. This completes imaging of one frame. Thereafter, similarly, high-speed imaging of a frame is repeated, so that the image sensor 20 completes imaging of a series of frames.

Although an example of the CMOS-type image sensor 20 has been described in the present embodiment, the image sensor 20 may be another type of imaging device. The image sensor 20 may be, for example, a CCD-type photodetector, a single-photon counting type element, or an amplification-type image sensor, such as an electron multiplying CCD (EMCCD) or intensified CCD (ICCD).

FIG. 1F is a diagram illustrating one example of an operation in one frame in the present embodiment. As illustrated in FIG. 1F, emission of the first pulsed light and emission of the second pulsed light may be alternately switched therebetween in one frame a plurality of times. Doing so makes it possible to reduce a time difference between the timings of acquiring detection images with two types of wavelength and makes it possible to perform photography with the first and second pulsed light at substantially the same time even when the user 1 is moving.

[1-3. Memory 25]

Biometric data indicating features of the body of the user 1 which are obtained or registered in advance is stored in the memory 25. The memory 25 may be built into the identifying device 100 or may be provided outside thereof. The memory 25 may be implemented by, for example, one or more ROMs, one or more optical discs, or one or more hard-disk drives.

The biometric data stored in the memory 25 may be, for example, an image of the user 1 or data that characterizes the image. The data that characterizes the image includes, for example, information indicating texture of the skin surface of the user 1, information indicating distribution of blood vessels of the user 1, or information indicating pits and bumps at a feature portion of the user 1. The "information indicating texture of the skin surface of the user 1" may be, for example, two-dimensional distribution of frequency components obtained by performing a Fourier transform on pixel values of two-dimensional distribution of wrinkles or minute pits and bumps at a portion on the skin surface of the user 1. This transform is effective when the wrinkles or the minute pits and bumps show a repetition of similar two-dimensional patterns. The "information indicating the distribution of blood vessels of the user 1" is, for example, image information indicating the distribution of veins of the user 1. The "information indicating pits and bumps at a feature portion of the user 1" is, for example, image information of the two-dimensional distribution of distances, the image information indicating pits and bumps at at least one of the orbit, the nose, the cheek, the cheekbone, the mouth, the jaw, the chin, and a part below the ear of the user 1. When the data that characterizes the image of the user 1 is stored, not only can unwanted information be eliminated to enhance the recognition accuracy, but also the amount of data that is stored can be reduced.

[1-4. Control Circuit 30 and Signal Processing Circuit 40]

The control circuit 30 causes the light source 10 to emit pulsed light with which the user 1 is illuminated. The control circuit 30 causes the image sensor 20 to detect at least part of reflected pulsed light that returns from the user 1. The control circuit 30 adjusts a time difference between the emission timing of the pulsed light of the light source 10 and the shutter timing of the image sensor 20. This time difference may hereinafter be referred to as a "phase" or a "phase delay". The "light-emission timing" of the light source 10 refers to a timing at which the pulsed light emitted by the light source 10 starts rising. The "shutter timing" refers to a timing at which the exposure is started. The control circuit 30 may adjust the phase by changing the light-emission timing or may adjust the phase by changing the shutter timing.

The control circuit 30 causes the image sensor 20 to output signals corresponding to intensity distribution of detected light and representing a two-dimensional image of the user 1. The control circuit 30 causes the signal processing circuit 40 to process the signals output from the image sensor 20. The control circuit 30 may be configured so as to remove offset components from signals detected by the individual pixels in the image sensor 20. The offset components are signal components resulting from external light or ambient light, such as the sunlight or a fluorescent lamp. In a state in which the light source 10 does not emit light, that is, in a state in which driving of the light source 10 is turned off, the image sensor 20 detects signals to thereby estimate offset components resulting from ambient light or external light.

The control circuit 30 can be, for example, a combination of a processor and a memory or an integrated circuit of a microcontroller or the like into which a processor and a memory are built. In the control circuit 30, for example, the processor executes a program recorded in the memory, to thereby perform adjustment of the light-emission timing and the shutter timing, the estimation of offset components, the removal of offset components, and so on.

The signal processing circuit 40 is a circuit for processing image signals output from the image sensor 20. The signal processing circuit 40 performs computational processing, such as image processing. The signal processing circuit 40 can be realized by, for example, a digital signal processor (DSP), a programmable logic device (PLD) such as a field programmable gate array (FPGA), or a combination of a central processing unit (CPU) or a graphics processing unit (GPU) and a computer program. The control circuit 30 and the signal processing circuit 40 may be an integrated circuit or may be separate individual circuits. Also, the signal processing circuit 40 may be, for example, a constituent element of an external device, such as a server provided at a remote location. In this case, the external device, such as a server, has a communication means to transmit/receive data to/from the light source 10, the image sensor 20, and the control circuit 30.

FIG. 1G is a flowchart illustrating an overview of operations performed by the control circuit 30. The control circuit 30 generally executes the operations illustrated in FIG. 1G. The description below will be given of operations for only detecting the internal scatter components I2 as one example. The control circuit 30 first causes the light source 10 to emit pulsed light for a predetermined time (step S101). At this point in time, the electronic shutter for the image sensor 20 is in a state in which charge accumulation is stopped. The control circuit 30 causes the electronic shutter to stop the charge accumulation until a period in which part of the pulsed light is reflected by the surface of the user 1 and reaches the image sensor 20 is completed. Next, the control circuit 30 causes the electronic shutter to start the charge accumulation at a timing at which other part of the pulsed light reaches the image sensor 20 after being scattered in the user 1 (step S102). After a predetermined time passes, the control circuit 30 causes the electronic shutter to stop the charge accumulation (step S103). Subsequently, the control circuit 30 determines whether or not the number of times the above-described charge accumulation was executed reaches a predetermined number of times (step S104). The predetermined number of times may be, for example, a thousand times to a hundred thousand times. If the result of the determination in step S104 is No, the control circuit 30 repeats steps S101 to S103 until the result of the determination becomes Yes. If the result of the determination in step S104 is Yes, the control circuit 30 causes the image sensor 20 to generate and output signals representing an image of two-dimensional distribution based on the total amount of signal charges accumulated in the floating diffusion layers in the respective pixels (step S105).

In the operations described above, components of light that are scattered inside a measurement target can be detected with high sensitivity. The plurality of light emissions and the plurality of exposures are not essential and are performed as appropriate. The operations in steps S101 to S105 illustrated in FIG. 1G can also be applied to a case in which only detection of the surface reflection components I1 is performed.

The control circuit 30 verifies the signals output from the image sensor 20 against the biometric data stored in the memory 25 to thereby authenticate the user 1. The operation of the control circuit 30 will be described below. The control circuit 30 causes the signal processing circuit 40 to generate image data, based on information obtained by the image sensor 20. The control circuit 30 compares the image data with the biometric data stored in the memory 25. When data that characterizes an image of the user 1 is stored in the memory 25, the signal processing circuit 40 extracts data that characterizes an image of the user 1, the image being based on the generated image data, and the control circuit 30 compares the extracted data with the data stored in the memory 25. Alternatively, the control circuit 30 may simply compare a feature in the information obtained by the image sensor 20 with a feature in pre-registered information. Also, the control circuit 30 may authenticate the user 1, based on users' features obtained by deep learning or machine learning using a support vector machine or the like.

[1-5. Optical System]

The identifying device 100 may include an image-forming optical system that forms a two-dimensional image of the user 1 on a light-receiving plane of the image sensor 20. An optical axis of the image-forming optical system is generally orthogonal to the light-receiving plane of the image sensor 20. The image-forming optical system may include a zoom lens. When the position of the zoom lens changes, the magnification factor of the two-dimensional image of the user 1 changes, and the resolution of the two-dimensional image on the image sensor 20 changes. Accordingly, even when the distance to the user 1 is large, the area to be measured can be magnified and be observed in detail.

Also, the identifying device 100 may include, between the user 1 and the image sensor 20, a bandpass filter for passing only light in the band of wavelengths emitted from the light source 10 or light close to the band. This makes it possible to reduce influences of disturbance components of ambient light and so on. The bandpass filter is constituted by a multilayer film filter or an absorbing filter. The bandwidth of the bandpass filter may be given a width of about 20 to 100 nm, considering the temperature of the light source 10 and band shift that occurs upon oblique incidence on the filter.

The identifying device 100 may include a polarizer between the light source 10 and the user 1 and a polarizer between the image sensor 20 and the user 1. In this case, the polarization direction of the polarizer arranged adjacent to the light source 10 and the polarization direction of the polarizer arranged adjacent to the image sensor 20 have a crossed-Nicols relationship. This can prevent specular reflection components, that is, components whose incident angle and reflection angle are the same, of the surface reflection components I1 of the user 1 from reaching the image sensor 20. That is, it is possible to reduce the amount of light with which the surface reflection components I1 reach the image sensor 20.

[2. Operation of Time-Resolved Imaging]

By performing time-resolved imaging, the identifying device 100 in the present embodiment can discriminate and detect the surface reflection components I1 and the internal scatter components I2.

The following description will be given of an example of the operation of the identifying device 100 in the present embodiment.

As illustrated in FIG. 1A, when the light source 10 illuminates the user 1 with pulsed light, the surface reflection components I1 and the internal scatter components I2 occur. Some of the surface reflection components I1 and the internal scatter components I2 reach the image sensor 20. The internal scatter components I2 pass through the inside of the user 1 before the pulsed light reaches the image sensor 20 after being emitted from the light source 10. That is, the optical path lengths of the internal scatter components I2 are larger than the optical path lengths of the surface reflection components I1. Accordingly, the time taken for the internal scatter components I2 to reach the image sensor 20 is delayed relative to the surface reflection components I1 on average.

In the time-resolved imaging, the surface reflection components I1 are obtained through an operation below.

Figure 2A:
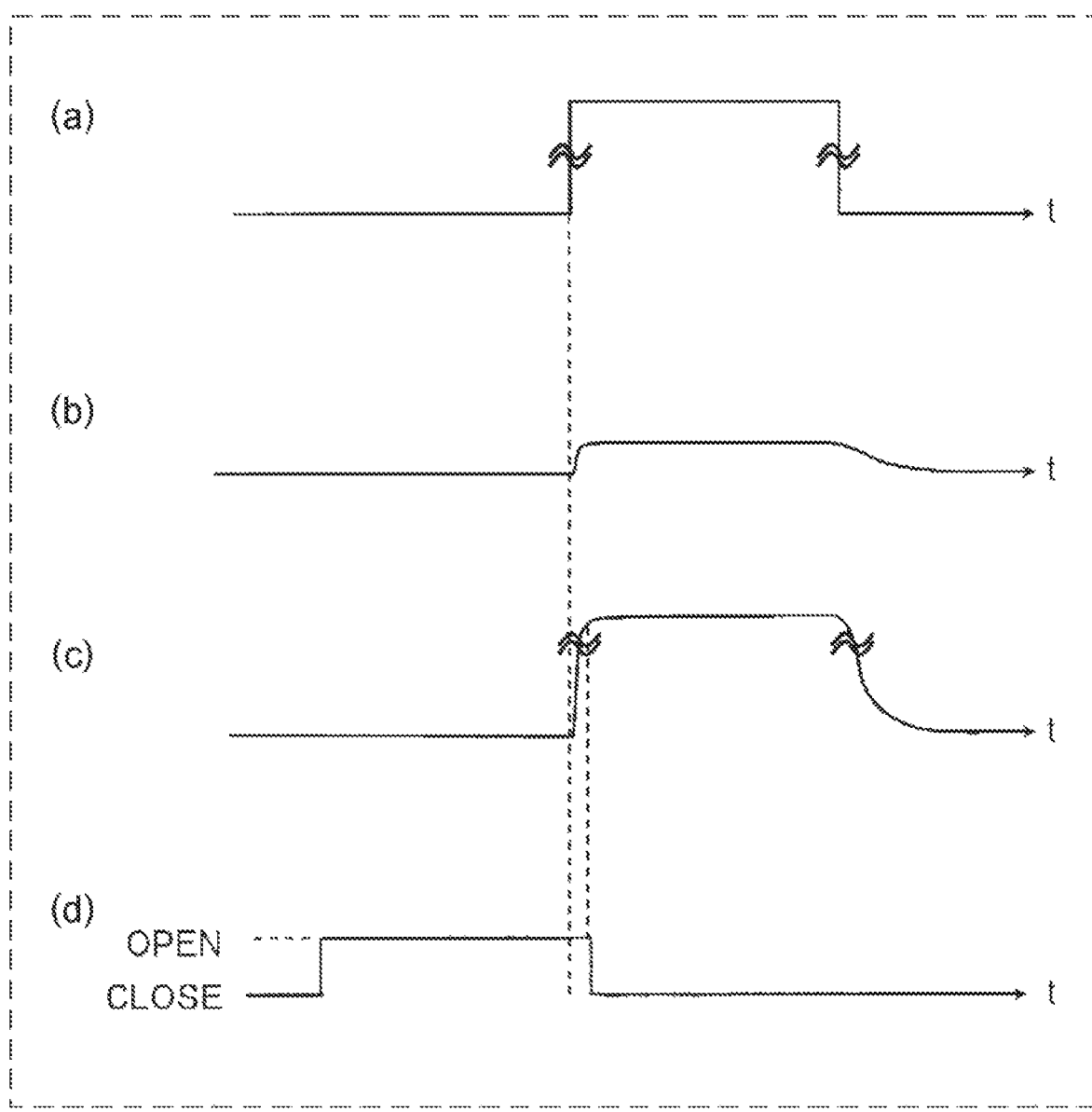
FIG. 2A is a diagram illustrating one example of optical signals resulting from light that returns from a user after rectangle pulsed light is emitted from a light source and that reaches the image sensor.

FIG. 2A is a diagram illustrating one example of optical signals resulting from light that returns from the user 1 after rectangle pulsed light is emitted from the light source 10 and that reaches the image sensor 20. In signals (a) to (d), the horizontal axis represents time (t). In signals (a) to (c), the vertical axis represents an intensity, and in signal (d), the vertical axis represents an "open" or "close" state of the electronic shutter. Signal (a) indicates the surface reflection components I1. Signal (b) indicates the internal scatter components I2. Signal (c) indicates combined components of the surface reflection components I1 (*a*) and the internal scatter components I2 (*b*). Signal (d) is a chart illustrating an electronic shutter timing for obtaining the surface reflection components I1 of the user 1.

As indicated by signal (d) in FIG. 2A, releasing the shutter allows components that reach the image sensor 20 earlier to be efficiently collected, the components being included in the reflected light that returns to the image sensor 20. The components that reach the image sensor 20 earlier are components resulting from less diffusion in the user 1 and includes surface information of the user 1. Although the amount of time in which light is substantially accumulated is a small amount of time at the leading edge of the pulse wave, the shutter does not necessarily have to be opened in that period. When charge is accumulated immediately before the shutter is closed, the shutter may be opened before the leading edge of the pulse wave reaches the image sensor 20, as indicated by signal (d) in FIG. 2A. This can eliminate the need for a high-cost imaging device having high temporal resolution on the order of picoseconds. The image sensor 20 in the identifying device 100 in the present embodiment can be implemented by a low-cost image sensor.

In order to execute the operation indicated by signal (d) in FIG. 2A, the control circuit 30 causes the image sensor 20 to detect components of at least part of reflected pulsed light in the rising period and to output signals indicating a two-dimensional image of the user 1. In the present embodiment, the signals output from the image sensor 20 can include signals obtained from the components of at least part of the reflected pulsed light in the rising period.

The light source 10 emits a rectangle pulse wave. In this case, the pulse duration does not necessarily have to be on the order of picoseconds and may be about a few nanoseconds. Thus, the light source 10 can be implemented by a low-cost light source. When the Tr characteristic at the leading edge of the pulse wave is steep, and only the leading edge is imaged by releasing the shutter, it is possible to minimize mixing unwanted internal scatter components I2 due to a time delay into an acquired image.

In the time-resolved imaging, the internal scatter components I2 can be obtained through an operation below.

Figure 2B:
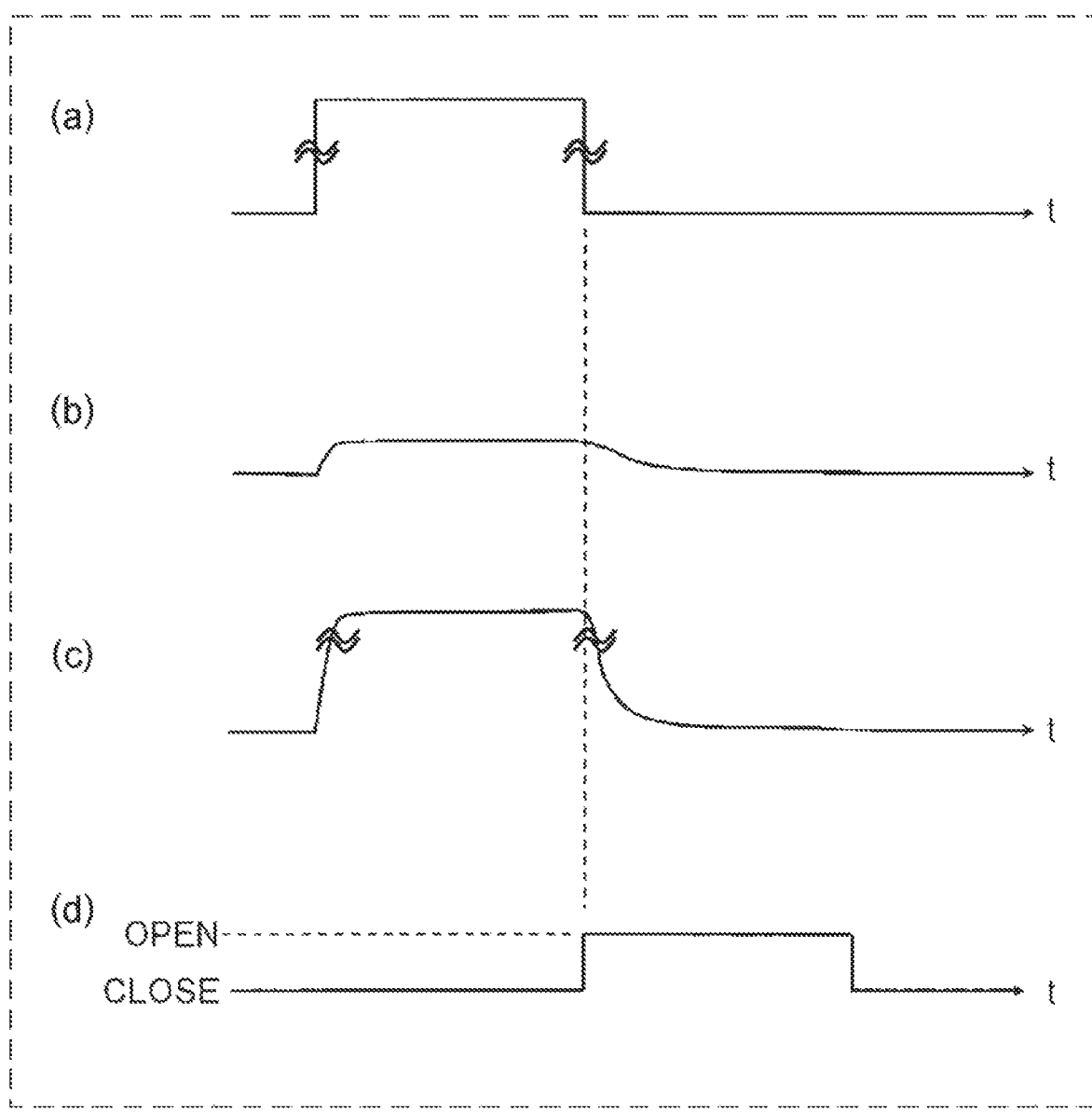
FIG. 2B is a diagram illustrating another example of optical signals resulting from light that returns from the user after the rectangle pulsed light is emitted from the light source and that reaches the image sensor.

FIG. 2B is a diagram illustrating another example of optical signals resulting from light that returns from the user 1 after the rectangle pulsed light is emitted from the light source 10 and that reaches the image sensor 20. Signals (a) to (c) in FIG. 2B indicate changes over time that are similar to signals (a) to (c) in FIG. 2A. Signal (d) in FIG. 2B indicates an electronic shutter timing for obtaining the internal scatter components I2.

As indicated by signal (a) in FIG. 2B, the surface reflection components I1 maintain a rectangle. On the other hand, since the internal scatter components I2 are a collection of light that has passed through various optical path lengths, they exhibit a characteristic like lingering at the trailing edge of the pulsed light, as indicated by signal (b) in FIG. 2B. That is, the internal scatter components I2 have a longer falling period than the surface reflection components I1. In order that the internal scatter components I2 are extracted at a high rate from the optical signal indicated by signal (c) in FIG. 2B, the electronic shutter starts charge accumulation at a point in time at or after the trailing edge of the surface reflection components I1, as indicated by signal (d) in FIG. 2B. The "point in time at or after the trailing edge of the surface reflection components I1" refers to a point in time at or after the surface reflection components I1 fall. The control circuit 30 adjusts the shutter timing for the charge accumulation. Since the identifying device 100 in the present embodiment discriminates and detects the surface reflection components I1 and the internal scatter components I2 that reach a deep part of the user 1, the duration of the pulsed light and the shutter duration are arbitrary. Accordingly, unlike a method using a conventional streak camera, the internal scatter components I2 can be obtained with a simple configuration, and cost can be significantly reduced.

In order to execute the operation indicated by signal (d) in FIG. 2B, the control circuit 30 causes the image sensor 20 to detect components of at least part of reflected pulsed light in the falling period and to output signals indicating a two-dimensional image of the user 1. In the present embodiment, the signals output from the image sensor 20 can include signals obtained from the components of at least part of the reflected pulsed light in the falling period.

In signal (a) in FIG. 2B, the trailing edge of the surface reflection components I1 falls perpendicularly. In other words, the time from when the surface reflection components I1 start falling until the surface reflection components I1 end the falling is zero. In practice, however, there are cases in which the trailing edge of the surface reflection components I1 does not fall perpendicularly, because of incomplete perpendicularity of the waveform of the pulsed light emitted by the light source 10, the presence of minute pits and bumps at the surface of the user 1, or diffusion in the epidermis. Also, since the user 1 is an opaque object, the amount of light of the surface reflection components I1 becomes much larger than that of the internal scatter components I2. Accordingly, even when the trailing edge of the surface reflection components I1 protrudes from its perpendicular falling position, it may be difficult to detect the internal scatter components I2. There are also cases in which ideal binary reading as indicated by signal (d) in FIG. 2B cannot be performed due to a time delay involved in electron transfer in the reading period of the electronic shutter. Accordingly, the control circuit 30 may slightly delay the shutter timing of the electronic shutter relative to a point in time that is immediately after falling of the surface reflection components I1. For example, the control circuit 30 may delay the shutter timing by about 0.5 to 5 ns. Instead of adjusting the shutter timing of the electronic shutter, the control circuit 30 may adjust the light-emission timing of the light source 10. The control circuit 30 adjusts a time difference between the shutter timing of the electronic shutter and the light-emission timing of the light source 10. When the shutter timing is overly delayed, the amount of the internal scatter components I2 which is inherently small decreases further. Thus, the shutter timing may be held at the vicinity of the trailing edge of the surface reflection components I1. Since a time delay due to diffusion in the user 1, the time delay being estimated based on the sensor sensitivity, is 4 ns, the maximum amount of delay of the shutter timing is about 4 ns.

The amount of detection light of the internal scatter components I2 may be amplified by the light source 10 emitting the pulsed light a plurality of times and performing exposure a plurality of times on the individual pulsed light at a shutter timing with the same phase.

Instead of or in addition to arranging the bandpass filter between the user 1 and the image sensor 20, the control circuit 30 may estimate offset components by performing photography for the same exposure time in a state in which the light source 10 does not emit light. The estimated offset components are removed from signals detected by the pixels in the image sensor 20. This makes it possible to eliminate external light and/or dark current components that occur on the image sensor 20.

Next, a description will be given of an example of a method for detecting the surface reflection components I1 and the internal scatter components I2 per frame.

FIG. 3A is one example of a timing chart when the surface reflection components I1 are detected. In order to detect the surface reflection components I1, for example, the shutter may be opened before the pulsed light reaches the image sensor 20, and the shutter may be closed before the trailing edge of the pulsed light reaches the image sensor 20, as illustrated in FIG. 3A. Controlling the shutter in such a manner makes it possible to reduce mixing of the internal scatter components I2. This also makes it possible to increase the rate of light that passes through the vicinity of the surface of the user 1. In particular, the timing of closing the shutter may be immediately after the light reaches the image sensor 20. Doing so makes it possible to perform signal detection in which the rate of the surface reflection components I1 whose optical path lengths are relatively small is increased. As another method for obtaining the surface reflection components I1, the entire pulsed light may be obtained by the image sensor 20, or continuous light may be emitted from the light source 10 and be detected by the image sensor 20.

Figure 3B:
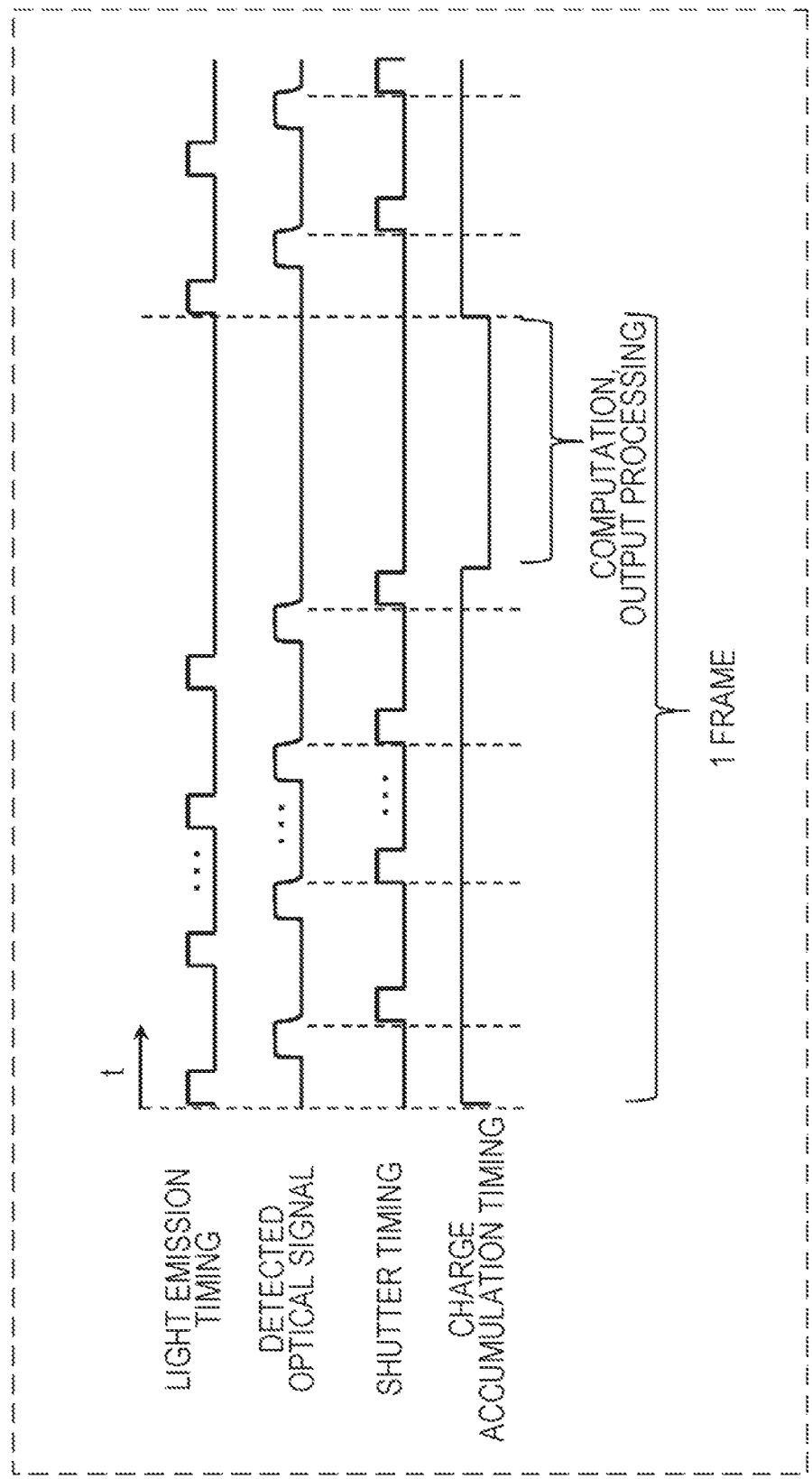
FIG. 3B is one example of a timing chart when internal scatter components are detected.

FIG. 3B is one example of a timing chart when the internal scatter components I2 are detected. Opening the shutter in a period in which the trailing edge of each pulse reaches the image sensor 20 makes it possible to obtain signals of the internal scatter components I2.

As in the present embodiment, when time-shared imaging using the same camera or the same sensor is performed, temporal and spatial displacement is less likely to occur. When signals of both the surface reflection components I1 and the internal scatter components I2 are obtained using the same sensor, components to be obtained may be switched for each frame, as illustrated in FIGS. 3A and 3B. Alternatively, components to be obtained may be alternately switched within one frame at high speed, as described above with reference to FIGS. 1D to 1F. In this case, it is possible to reduce a detection time difference between the surface reflection components I1 and the internal scatter components I2.

In addition, respective signals of the surface reflection components I1 and the internal scatter components I2 may be obtained using light having two wavelengths. When the surface reflection components I1 and the internal scatter components I2 are each obtained with two wavelengths, for example, a method in which four types of charge accumulation are switched at high speed within one frame can be utilized, as described above with reference to FIGS. 1D to 1F. With such a method, it is possible to reduce temporal displacement of detection signals.

[3. Operation of Space-Resolved Imaging]

The surface reflection components I1 and the internal scatter components I2 can each be obtained by space-resolved imaging, other than the above-described time-resolved imaging.

Figure 4A:
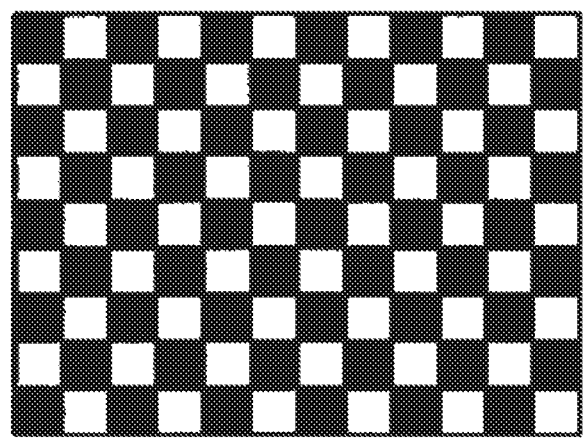
FIG. 4A is a view schematically illustrating one example of distribution of two-dimensional pattern light that the light source projects to the user.
Figure 4B:
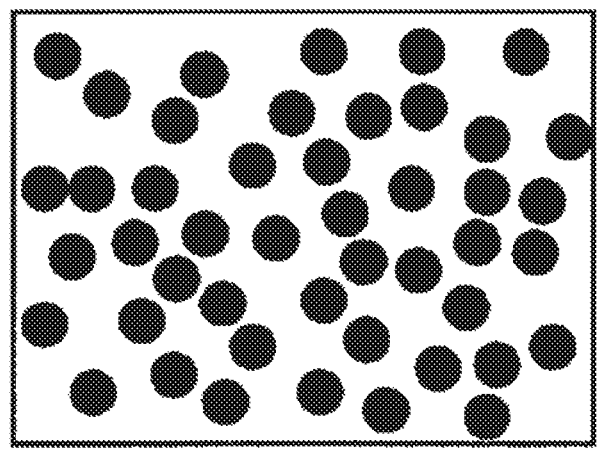
FIG. 4B is a view schematically illustrating another example of the distribution of the two-dimensional pattern light that the light source projects to the user.
Figure 4C:
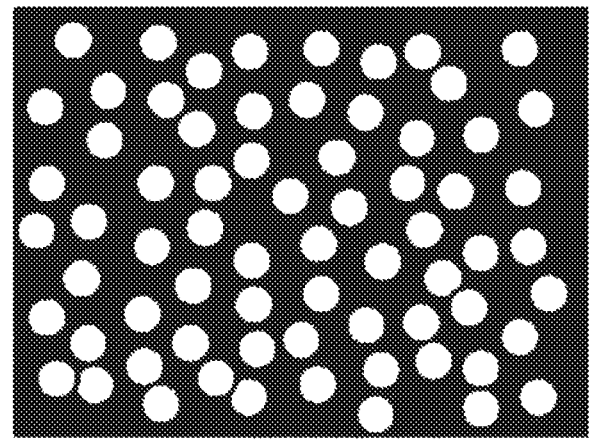
FIG. 4C is a view schematically illustrating yet another example of the distribution of the two-dimensional pattern light that the light source projects to the user.

FIGS. 4A to 4C are diagrams schematically illustrating examples of distribution of two-dimensional pattern light that the light source 10 projects to the user 1. In the examples illustrated in FIGS. 4A to 4C, white portions represent bright portions where light exists, and black portions represent dark portions where no light exists. FIG. 4A illustrates a checkered pattern in which bright portions and dark portions are cyclically distributed. FIG. 4B illustrates a dot pattern in which dark portions are randomly distributed in a bright portion. FIG. 4C illustrates a dot pattern in which bright portions are randomly distributed in a dark portion.

The control circuit 30 causes the light source 10 to emit two-dimensional pattern light to project two-dimensional pattern light to the user 1. As illustrated in FIGS. 4A to 4C, the two-dimensional pattern light includes at least one bright portion and at least one dark portion. The two-dimensional pattern light can be obtained by, for example, disposing a light-shielding mask having two-dimensional distribution in front of the light source 10. Alternatively, the two-dimensional pattern light may be formed using a digital micro-mirror device (DMD) or a spatial light modulator (SLM). The two-dimensional pattern light may be continuous light or pulsed light.

As illustrated in FIGS. 4A to 4C, the light source 10 emits two-dimensional pattern light whose intensity is spatially modulated, such as a checkered pattern or a dot pattern. When the two-dimensional pattern light is projected to the user 1, a large amount of light returns from bright portions and a small amount of light returns from dark portions. Reflected light that returns from the dark portions includes the internal scatter components I2 diffused inside the user 1 and include almost no surface reflection components I1.

In order to detect the internal scatter components I2 by using the two-dimensional pattern light, the control circuit 30 causes the image sensor 20 to detect at least part of the reflected light that returns from at least one dark portion of the user 1 to which the two-dimensional pattern light is projected and to output signals corresponding to the intensity distribution of the at least part of the detected reflected light. With this arrangement, when the two-dimensional pattern light is pulsed light, it is possible to obtain a part from the leading edge to the trailing edge of the internal scatter components I2, the part being indicated by signal (b) in FIG. 2A or FIG. 2B. In the present embodiment, signals output from the image sensor 20 can include the above-described signals obtained from at least one dark portion.

On the other hand, reflected light that returns from bright portions include both the surface reflection components I1 and the internal scatter components I2. Thus, the surface reflection components I1 can be calculated by subtracting detection data obtained from dark portions from detection data obtained from bright portions adjacent thereto. In this case, the spatial resolution decreases. One possible example of measures against the decrease in the spatial resolution is obtaining signals a plurality of times by shifting the distribution of two-dimensional pattern light or changing the distribution itself of the two-dimensional pattern light, rather than obtaining signals with a single shot. This makes it possible to obtain the surface reflection components I1 without reducing the spatial resolution.

In order to detect the surface reflection components I1 by using the two-dimensional pattern light, the control circuit 30 causes the image sensor 20 to detect at least part of reflected light that returns from at least one dark portion of the user 1 to which the two-dimensional pattern light is projected and at least part of reflected light that returns from at least one bright portion of the user 1. The control circuit 30 causes the image sensor 20 to output signals corresponding to the intensity distribution of the at least part of the reflected light that returns from the at least one dark portion and signals corresponding to the intensity distribution of the at least part of the reflected light that returns from the at least one bright portion. The control circuit 30 causes the signal processing circuit 40 to calculate the surface reflection components I1 by subtracting the above-described signals obtained from the at least one dark portion from the above-described signals obtained from the at least one bright portion. Thus, when the two-dimensional pattern light is pulsed light, it is possible to obtain the part from the leading edge to the trailing edge of the surface reflection components I1, the part being indicated by signal (a) in FIG. 2A or 2B. In the present embodiment, the signals output from the image sensor 20 can include the above-described signals obtained from at least one bright portion, in addition to the above-described signals obtained from at least one dark portion.

The space-resolved imaging and the time-resolved imaging may be combined to obtain each of the surface reflection components I1 and the internal scatter components I2.

When the two-dimensional pattern light is pulsed light, the surface reflection components I1 may be obtained by detecting at least part of reflected pulsed light in the rising period, the reflected pulsed light returning from at least one bright portion. Similarly, the internal scatter components I2 may be obtained by detecting at least part of reflected pulsed light in the falling period, the reflected pulsed light returning from at least one bright portion or at least one dark portion. Operations of the control circuit 30 and the signal processing circuit 40 during detection of components of the reflected pulsed light in the rising period and components of the reflected pulsed light in the falling period are substantially the same as those described above.

[4. Biometric Authentication Using Surface Reflection Components I1 and Biometric Authentication Using Internal Scatter Components I2]

A specific example of biometric authentication performed by the identifying device 100 in the present embodiment will be described in comparison with a method using an ordinary camera.

FIG. 5A is a diagram schematically illustrating a state in which a user 1 is photographed with an ordinary camera 90. Light that illuminates the user 1 penetrates the surface of the user 1 to a depth of a few millimeters. Thus, the ordinary camera 90 detects both the surface reflection components I1 and the internal scatter components I2 included in reflected light that returns from the user 1. There is a possibility that an image that includes both the surface reflection components I1 and the internal scatter components I2 is slightly blurred. Thus, in face-based authentication using the ordinary camera 90, the false acceptance rate or the false rejection rate may increase. Possible examples include falsely identifying one of identical twins as the other twin or falsely identifying a person who changed his or her hair style as another person. That is, with the method using the ordinary camera 90, the accuracy of face-based authentication can deteriorate.

FIG. 5B is a diagram schematically illustrating one example of photography of the user 1 by using the surface reflection components I1 in the present embodiment. In the identifying device 100 in the present embodiment, the surface reflection components I1 can be detected by the time-resolved imaging or the space-resolved imaging, as described above. This makes it possible to more clearly detect texture of the skin surface of the user 1. Examples of the texture include wrinkles or minute pits and bumps. Use of a result obtained by verifying the information obtained from the surface reflection components I1 against the information included in the biometric data in the memory 25 and indicating the texture of the skin surface of the user 1 makes it possible to enhance the authentication accuracy in. As a result, the false rejection rate or the false acceptance rate decreases.

Figure 5C:
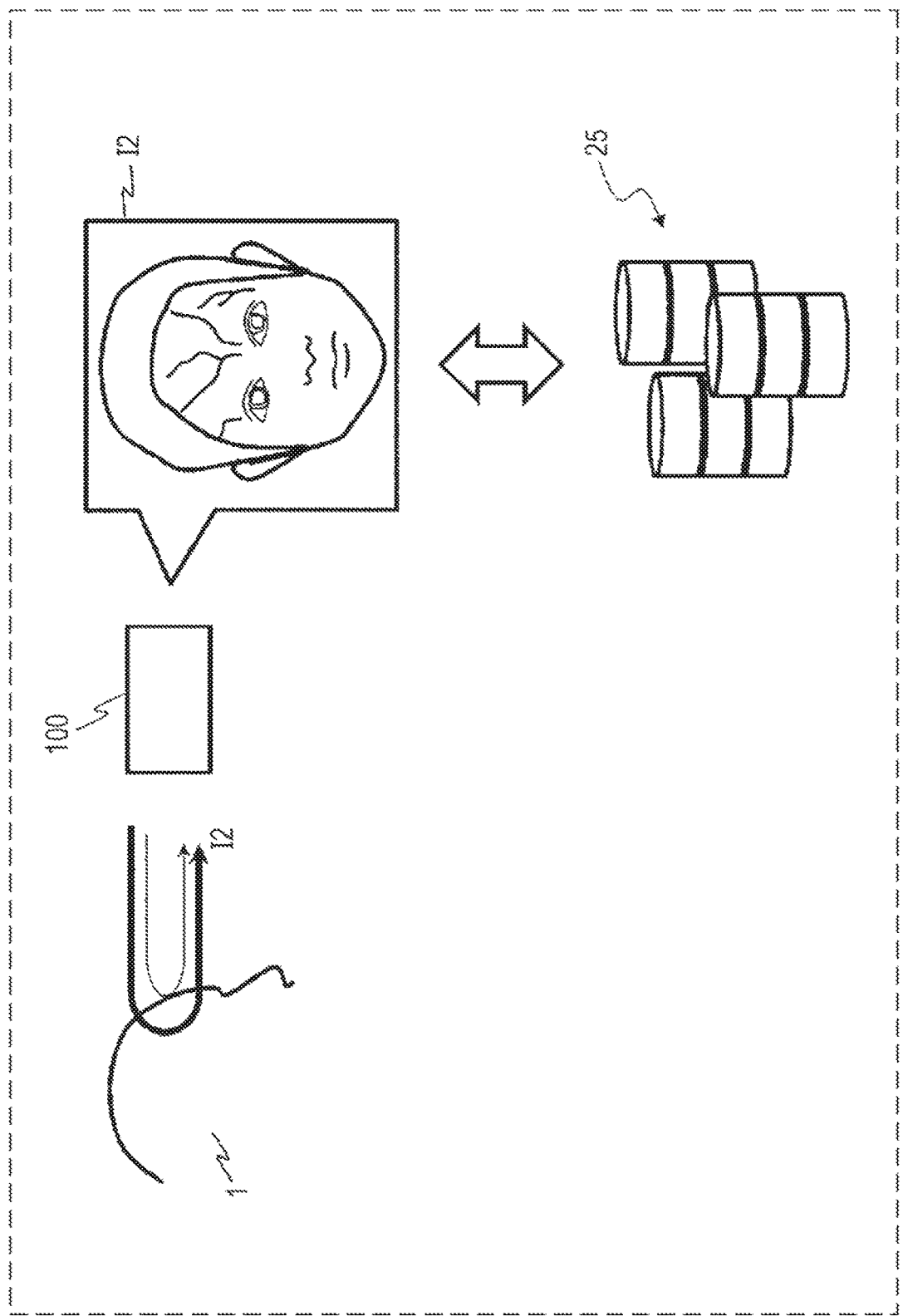
FIG. 5C is a diagram schematically illustrating one example of photography of the user by using the internal scatter component in the present embodiment.

FIG. 5C is a diagram schematically illustrating one example of photography of the user 1 by using the internal scatter components I2 in the present embodiment. The identifying device 100 in the present embodiment can detect the internal scatter components I2 by using the time-resolved imaging or the space-resolved imaging, as described above. This makes it possible to more clearly detect the distribution of blood vessels, such as veins, of the user 1. Use of a result obtained by verifying the information obtained from the internal scatter components I2 against the information included in biometric data of the memory 25 and indicating the distribution of the blood vessels of the user 1 makes it possible to enhance the authentication accuracy. As a result, the false rejection rate or the false acceptance rate decreases.

Authentication using the surface reflection components I1 and authentication using the internal scatter components I2 may be combined together. For example, depending on the application, authentication may be regarded as being successful only when passing both the authentications or may be regarded as being successful when passing one of the authentications. When the internal scatter components I2 are used for vein-based authentication, near infrared that can more easily penetrate the living body may be used. When the surface reflection components I1 are used for face-based authentication, short-wavelength light in a blue range or the like that hardly penetrates the living body may be used. As described above, different types of wavelength light may be used to detect the surface reflection components I1 and the internal scatter components I2.

The internal scatter components I2 include biometric information about a deeper portion of the user 1 than the surface reflection components I1. Thus, the internal scatter components I2 makes it possible to obtain information of veins, inner cells, and so on, that is different from the information obtained using the surface reflection components I1. This makes it possible to execute a plurality of different types of authentication, for example, face-based authentication mainly using the surface reflection components I1 and vein-based authentication mainly using the internal scatter components I2. Even when one of the authentications fails, the other authentication can compensate for the failure of that authentication. This leads to reliable high-accuracy authentication, thus making it possible to ensure higher security. Also, when a person other than the user impersonates the user 1, the other person needs to go through both the authentications, which makes falsification very difficult. Thus, the identifying device 100 in the present embodiment can realize an authentication system that makes forgery or falsification more difficult.

Also, other than executing a plurality of types of authentication independently from each other, authentication based on machine learning may be performed using data resulting from combining the surface reflection components I1 and the internal scatter components I2 together. Since the data includes different features to thereby increase the amount of information, it is possible to improve the accuracy rate of recognition based on machine learning.

In addition, a ToF method for calculating the distance to an object based on a round-trip time of pulsed light may be used to authenticate the user 1. Use of the ToF method can obtain two-dimensional distribution of distances between the image sensor 20 and a surface of the user 1. The two-dimensional distribution of distances between the image sensor 20 and the surface of the user 1 can be said to be three-dimensional distribution of the surface of the user 1.

A distances d between the image sensor 20 and the surface of the user 1 can be given by:

$$d = c\tau/2$$

where $\tau$ represents a round-trip time from when the pulsed light is emitted by the light source 10 until light reflected by the surface of the user 1 is detected by the image sensor 20, and c represents the speed of light in the air.

A direct ToF method and an indirect ToF method are available as methods for obtaining the round-trip time $\tau$.

In the direct ToF method, the round-trip time $\tau$ of light is directly measured to calculate the distance d to an object. In the direct ToF method, a temporal resolution for achieving a distance resolution of $\Delta d = 1$ mm is given by $\Delta\tau = 2\Delta d/c \approx 6.6$ ps. Thus, in the direct ToF method, high-speed imaging having a temporal resolution in picoseconds can be used in order to achieve a distance resolution in millimeters.

In an indirect ToF method that is practically used, the round-trip time $\tau$ of pulsed light is measured based on a phase difference in the reflected pulsed light to calculate the distance d to an object. The phase difference in the reflected pulsed light corresponds to a time lag between the emitted pulsed light and the reflected pulsed light. In the indirect ToF method, a decrease in the pulse duration $\Delta t$ does not necessarily mean an increase in the measurement accuracy. In the indirect ToF method, the light intensity of emitted light is generally modulated with a rectangular wave or a sine wave in order to detect the phase difference.

Figure 6:
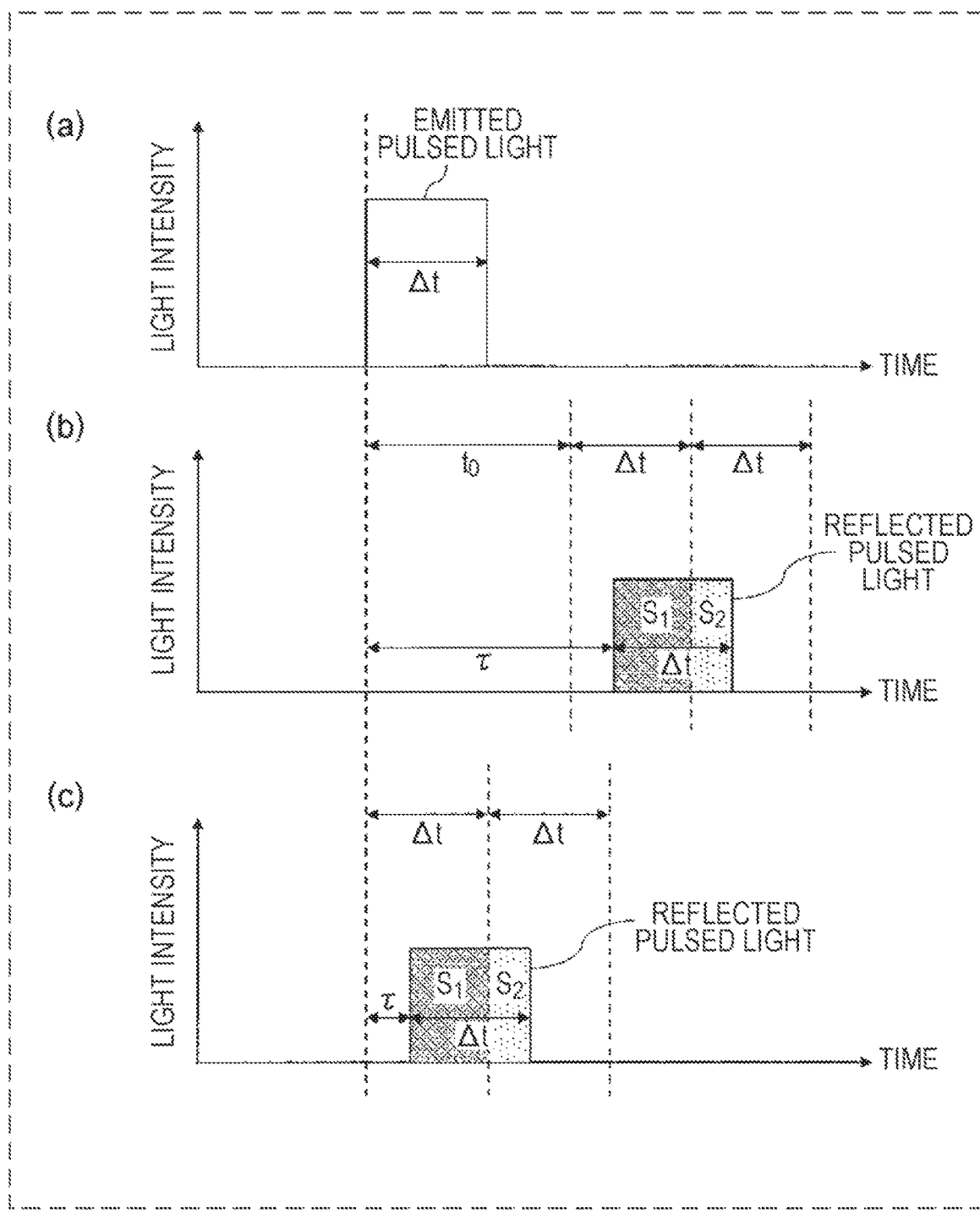
FIG. 6 is a diagram illustrating a principle for measuring the round-trip time of pulsed light by using an indirect time-of-flight (ToF) method.

FIG. 6 is a diagram illustrating a principle for measuring the round-trip time $\tau$ of pulsed light by using the indirect ToF method. Signal (a) in FIG. 6 indicates changes in the intensity of emitted pulsed light over time, and signals (b) and (c) in FIG. 6 indicate changes in the intensity of reflected pulsed light over time.

In the example indicated by signal (a) in FIG. 6, the intensity of the emitted pulsed light is modulated with a rectangular wave. In order to measure the phase difference with high accuracy, the intensity of the emitted pulsed light is basically modulated with a speed of an order magnitude that is approximately the same as that of the round-trip time $\tau$ of light.

The image sensor 20 can detect the phase difference in the pulsed light by opening the electronic shutter and measuring the intensity. In the example indicated by signal (b) in FIG. 6, the image sensor 20 opens the electronic shutter when a time $t_0$ passes after the pulsed light is emitted and starts detecting reflected pulsed light. The time $t_0$ is longer than the pulse duration $\Delta t$ of the pulsed light and is shorter than the round-trip time $\tau$ of light. That is, $\Delta t < t_0 < \tau$ is given. After opening the electronic shutter, the image sensor 20 accumulates signal charge corresponding to the amount of reflected pulsed light for each period of time $\Delta t$. The difference between the round-trip time $\tau$ of light and the time $t_0$ is equal to $[S_2/(S_1+S_2)]\Delta t$, where $S_1$ represents the amount of signal charge accumulated during a first period of time $\Delta t$, and $S_2$ represents the amount of signal charge accumulation during a next period of time $\Delta t$. Thus, the round-trip time $\tau$ of light is given by $\tau = t_0 + [S_2/(S_1+S_2)]\Delta t$. The distance d to an object can be calculated from the round-trip time $\tau$ of light which is indirectly obtained from the amounts of accumulated signal charges $S_1$ and $S_2$.

In the example indicated by signal (c) in FIG. 6, the reflected pulsed light returns to the image sensor 20 before the emission of the pulsed light is finished. That is, $\tau < \Delta t$ is given. In this case, simultaneously with the emission of the pulsed light from the light source 10, the image sensor 20 opens the electronic shutter and accumulates signal charge corresponding to the amount of reflected pulsed light for each period of time $\Delta t$. The round-trip time of light is given by $\tau = [S_2/(S_1+S_2)]\Delta t$.

In the ToF method, the control circuit 30 causes the image sensor 20 to detect at least part of reflected pulsed light and to output signals indicating three-dimensional distribution of the surface of the user 1. In the present embodiment, the signals output from the image sensor 20 can include signals indicating three-dimensional distribution of the surface of the user 1.

When the surface reflection components I1 included in at least part of the reflected pulsed light are used in the ToF method, it is possible to more clearly detect the three-dimensional distribution of the surface of the user 1, the three-dimensional distribution including wrinkles or minute pits and bumps, compared with conventional ToF methods.

In the direct ToF method, it is possible to detect the distance to an object by detecting the surface reflection components I1 included in the rising period of the reflected pulsed light. In the indirect ToF method, the part from the leading edge to the trailing edge of the reflected pulsed light is detected, as indicated by signals (b) and (c) in FIG. 6, to calculate the distance to an object. When the space-resolved imaging is used, the part from the leading edge to the trailing edge of the surface reflection components I1 can be separated from the reflected pulsed light.

Also, when the space-resolved imaging is used, the part from the leading edge to the trailing edge of the internal scatter components I2 can be obtained from the reflected pulsed light. When the part from the leading edge to the trailing edge of the internal scatter components I2 is used in the indirect ToF method, it is possible to obtain the two-dimensional distribution of distances between the image sensor 20 and blood vessels of the user 1, that is, it is possible to obtain the three-dimensional distribution of the blood vessels of the user 1.

Figure 7:
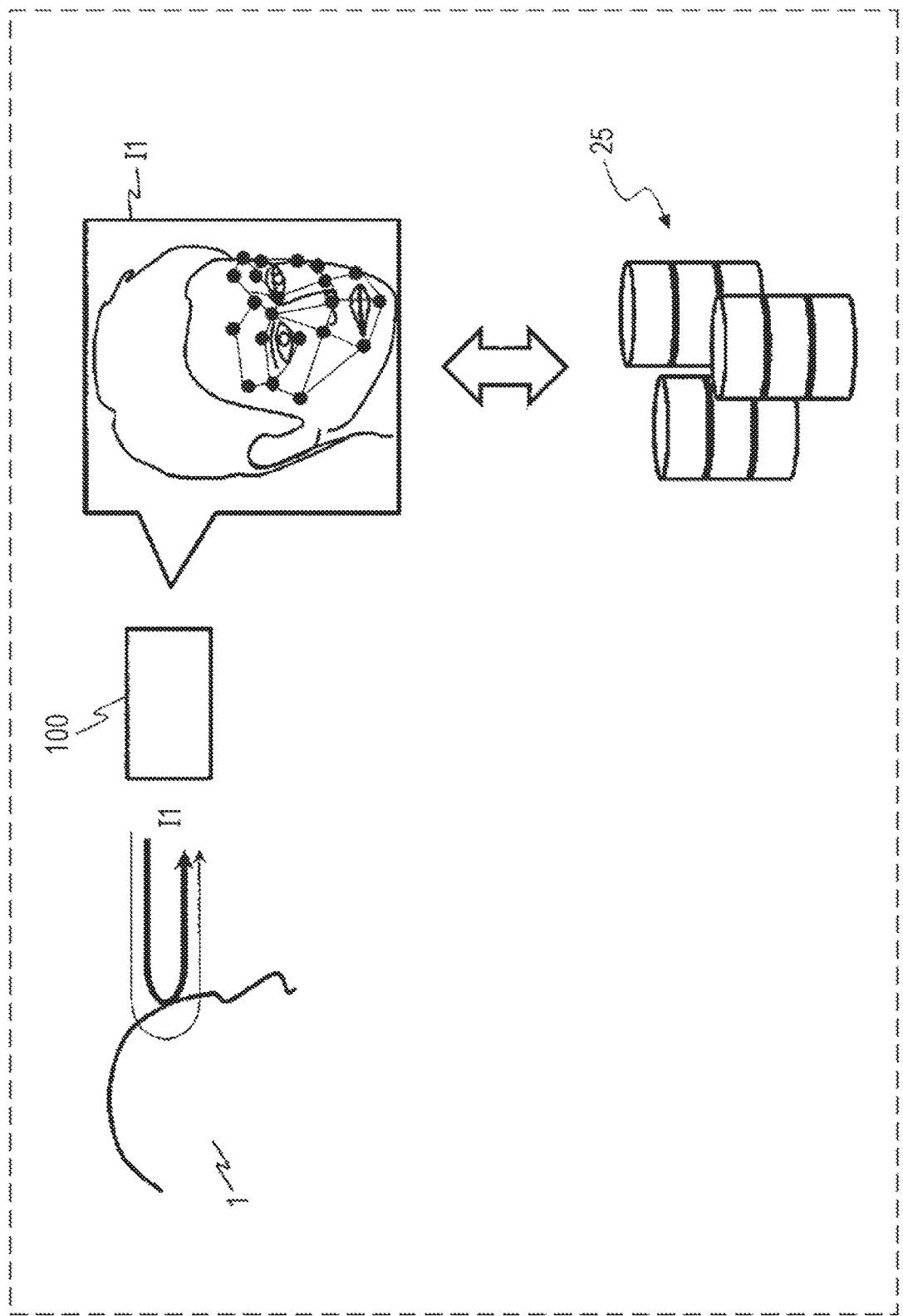
FIG. 7 is a view schematically illustrating one example of photography of a user by using a ToF method in the present embodiment.

FIG. 7 is a view schematically illustrating one example of photography of a user 1 by using a ToF method in the present embodiment. In the example illustrated in FIG. 7, three-dimensional distribution of a surface of the user 1 is calculated from the surface reflection components I1. Use of a result obtained by verifying information obtained from the three-dimensional distribution of the surface of the user 1 against information included in the biometric data in the memory 25 and indicating pits and bumps of a feature portion of the user 1 makes it possible to enhance the authentication accuracy. As a result, the false rejection rate or the false acceptance rate decreases. The three-dimensional distribution of the surface of the user 1 may be calculated from reflected pulsed light including both the surface reflection components I1 and the internal scatter components I2.

Next, a description will be given of a series of processes for biometric authentication of the user 1 which uses the identifying device 100 in the present embodiment.

Figure 8:
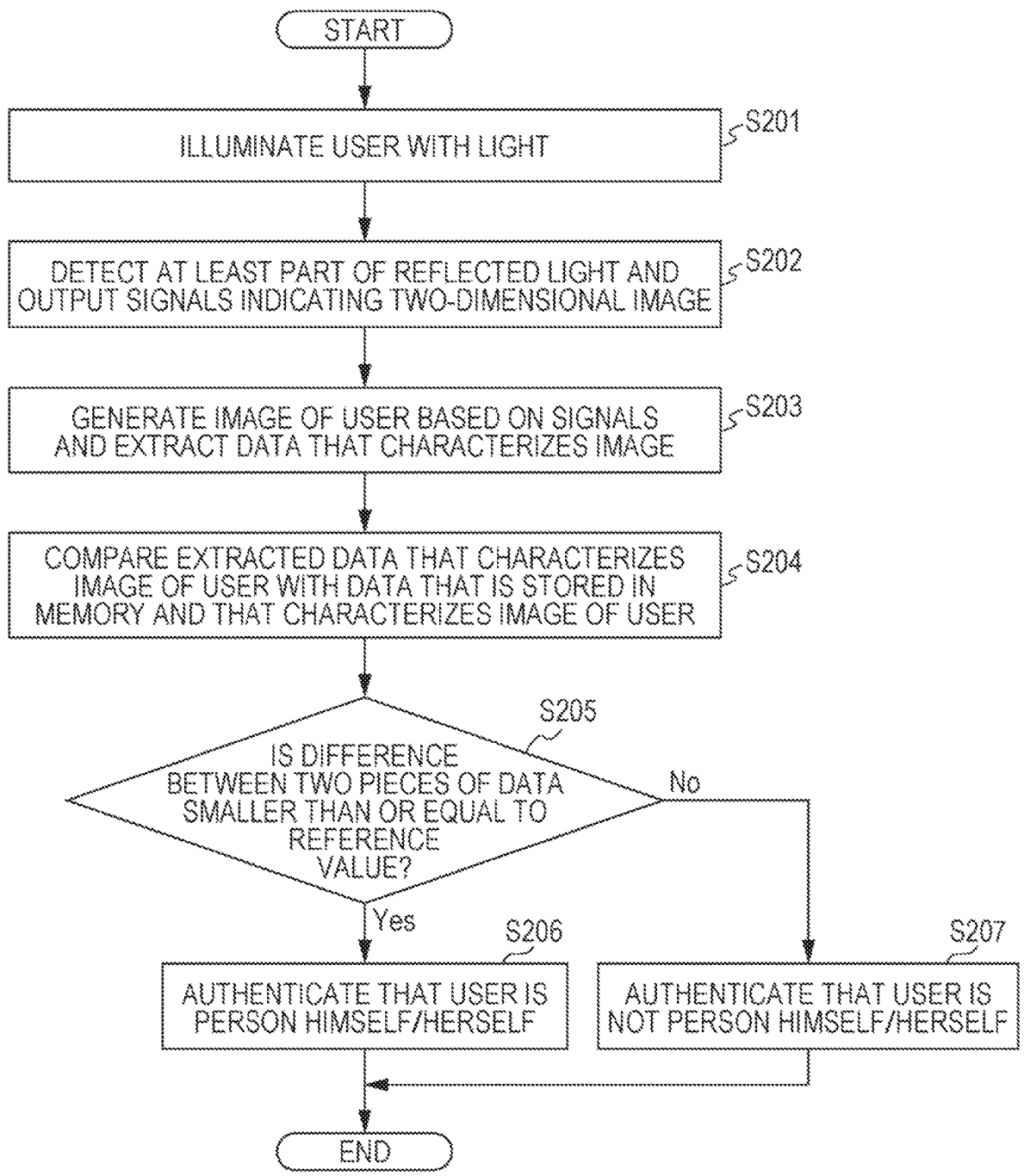
FIG. 8 is a flowchart illustrating one example of processing executed by the control circuit.

FIG. 8 is a flowchart illustrating one example of processes executed by the control circuit 30.

In step S201, the control circuit 30 causes the light source 10 to illuminate the user 1 with light. For time-resolved imaging, the light is pulsed light, and for space-resolved imaging, the light is two-dimensional pattern light. For a combination of time-resolved imaging and space-resolved imaging, the light is two-dimensional pattern light and pulsed light.

In step S202, the control circuit 30 causes the image sensor 20 to detect at least part of reflected light that returns from the user 1 and to output signals corresponds to the intensity distribution of the detected light and indicating a two-dimensional image of the user 1. When the reflected light is pulsed light, the at least part of the reflected light corresponds to, for example, components of the pulsed light in the rising period or components of the pulsed light in the falling period. The surface reflection components I1 are obtained from the components in the rising period, and the internal scatter components I2 are obtained from the components in the falling period. Of the reflected pulsed light, a part from the leading edge to the trailing edge of the surface reflection components I1 or a part from the leading edge to the trailing edge of combined components of the surface reflection components I1 and the internal scatter components I2 is detected, when the indirect ToF method is used to obtain the three-dimensional distribution of a surface of the user 1.

In step S203, the control circuit 30 causes the signal processing circuit 40 to generate an image of the user 1, based on the signals output by the control circuit 30, and extracts data that characterizes the image. The data that characterizes the image generated based on the surface reflection components I1 includes information indicating texture of a skin surface of the user 1. The data that characterizes the image generated based on the internal scatter components I2 includes information indicating the distribution of blood vessels of the user 1. For the ToF method, the data that characterizes the image generated based on the surface reflection components I1 or the data that characterizes the image generated based on the combined components of the surface reflection components I1 and the internal scatter components I2 includes information indicating the three-dimensional distribution of the surface of the user 1, that is, information indicating pits and bumps at a feature portion of the user 1.

In step S204, the control circuit 30 compares the data that is extracted from the generated image of the user 1 and that characterizes the image with data that is stored in the memory 25 and that characterizes an image of the user 1.

In step S205, the control circuit 30 determines whether or not a difference between the compared two pieces of data is smaller than or equal to a reference value. For example, when the information on the three-dimensional distribution of the surface of the user 1, the information being obtained by the ToF method, is compared with the information indicating the pits and bumps of the feature portion of the user 1, the information being included in the biometric data, an example of a criterion for the determination is as follows. With respect to all measurement points on the surface of the user 1 or measurement points larger than or equal to a certain ratio, such as 80%, the control circuit 30 evaluates whether or not the difference between the above-described two pieces of data is smaller than or equal to the reference value.

If the difference between the two pieces of data is smaller than or equal to the reference value, the control circuit 30 determines that the user 1 is the person himself or herself in step S206. When the difference is larger than the reference value, the control circuit 30 determines that the user 1 is not the person himself or herself in step S207.

The identifying device 100 in the present embodiment can realize biometric authentication of the user 1 in a contactless manner. Accordingly, the amount of load on the user 1 during the authentication is small.

Of portions of the body of the user 1, a portion other than the face may be used for the authentication. Examples of the other portion include a hand. For example, the surface reflection components I1 may be obtained from a fingerprint, or the internal scatter components I2 may be obtained from veins of a finger. Since hands are likely to clearly show individual-specific fingerprints or veins, use of the hands improves the recognition accuracy. When the target portion is a hand of the user 1, the user 1 may place his or her hand on a glass plate to suppress or reduce his or her body movement. In this case, when space exists between the glass plate and the identifying device 100, there is an advantage that the focal point of the camera can be adjusted. Also, in the case of hand-based authentication, when the light source 10 emits an amount of light that exceeds class 1, it is possible to enhance the S/N ratio of detection signals on the image sensor 20.

Next, a description will be given of an application example of the identifying device 100 in the present embodiment.

Figure 9:
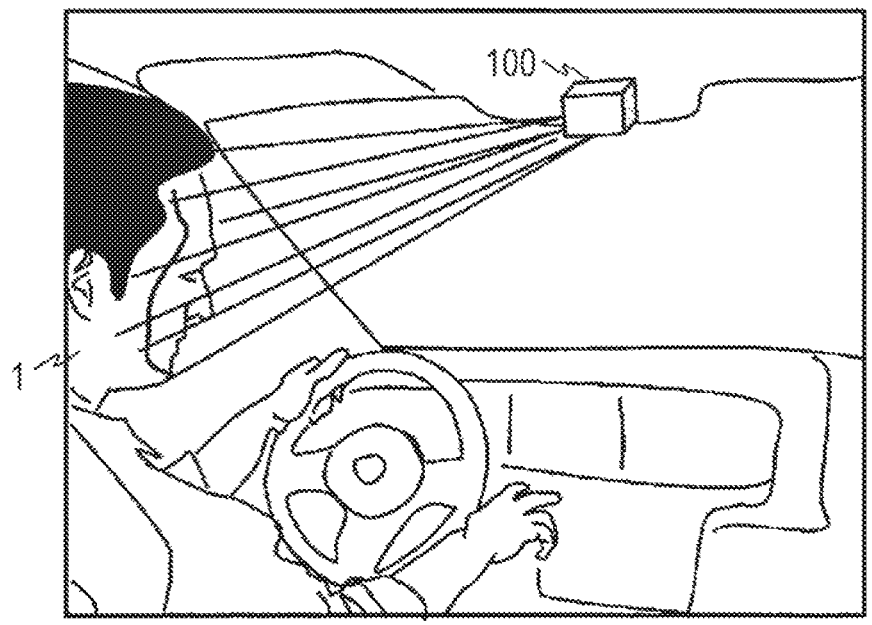
FIG. 9 is a view schematically illustrating one example in which the identifying device in the present embodiment is installed in a cabin of a vehicle.

FIG. 9 is a view schematically illustrating one example in which the identifying device 100 in the present embodiment is installed in a cabin of a vehicle. As illustrated in FIG. 9, the identifying device 100 provided in the cabin may identify a driver, that is, a user 1. The vehicle may be started upon identification of the user 1 by the identifying device 100, instead of using a key of the vehicle. The identifying device 100 may identify a passenger during automated driving and feed back a result of the identification to the automated driving, which is customized according to the passenger. In response to the feedback, for example, the brake may be gently actuated when the passenger is a senior, or the vehicle may be driven in a more exhilarating driving mode when the passenger is a person who likes driving. This makes it possible to perform automated driving that suits each individual.

Figure 10:
FIG. 10 is a view schematically illustrating one example in which the identifying device in the present embodiment is applied to a mobile terminal.

FIG. 10 is a view schematically illustrating one example in which the identifying device 100 in the present embodiment is applied to a mobile terminal. The mobile terminal is, for example, a smartphone, a tablet computer, or a personal computer. The image sensor 20 in the identifying device 100 may be an image sensor built into the mobile terminal.

The identifying device 100 in the present embodiment may also be applied to, for example, an automated teller machine (ATM) installed at a bank or a convenience stores or an entryway of a house, other than a vehicle or a mobile terminal.

The identifying device 100 in the present embodiment can perform high-accuracy authentication including a combination two or more authentications. The identifying device 100 in the present embodiment can be used not only for authentication for login to a terminal but also for security authentication using a terminal. Examples of the security authentication using a terminal include login to a bank account after login to the terminal and authentication for login to accounts of various services. Conventional password authentication may also be used together to provide a system in which the authentication in the present disclosure is additional authentication. This makes it possible to reduce the risk of hacking and can ensure higher security, compared with a system in which only conventional password authentication is performed.

The present disclosure also includes a method including the operations executed by the control circuit 30 and the signal processing circuit 40.

As described above, the present disclosure includes an identifying device and an identifying method recited in the following items.

[Item 1]

An identifying device according to a first item includes a light source; an image sensor; a memory that stores therein biometric data indicating a feature of a body of a user; and a processor. The processor causes the light source to emit pulsed light having a pulse duration of more than or equal to 0.2 ns and less than or equal to 1 μs to illuminate the user with the pulsed light, causes the image sensor to detect at least part of reflected pulsed light that returns from the user and to output a signal corresponding to two-dimensional distribution of an intensity of the at least part of the reflected pulsed light, and verifies the signal against the biometric data to identify the user.

[Item 2]

In the identifying device according to the first item, the pulse duration of the pulsed light may be more than or equal to 3 ns and less than or equal to 50 ns.

[Item 3]

In the identifying device according to the first or second item, the image sensor may include pixels; the processor may cause the image sensor to repeatedly accumulate charges in each of the pixel a thousand times to a hundred thousand times, the charges corresponding to the intensity of the at least part of the reflected pulsed light; and the signal may indicate two-dimensional distribution of a total amount of the charges accumulated in the pixels.

[Item 4]

In the identifying device according to one of the first to third items, the biometric data may include first information indicating texture of a skin surface of the user.

[Item 5]

In the identifying device according to the fourth item, the processor may cause the image sensor to obtain a first signal by detecting components of at least part of the reflected pulsed light in a rising period and to output the first signal, the rising period being a period from start to end of an increase of an intensity of the reflected pulsed light, and may verify information obtained from the first signal against the first information to identify the user.

[Item 6]

In the identifying device according to one of the first to fifth items, the biometric data may include second information indicating distribution of blood vessels of the user.

[Item 7]

In the identifying device according to the sixth item, the processor may cause the image sensor to obtain a second signal by detecting a component of at least part of the reflected pulsed light in a falling period and to output the second signal, the falling period being a period from start to end of a decrease of an intensity of the reflected pulsed light, and may verify information obtained from the second signal against the second information to identify the user.

[Item 8]

In the identifying device according to one of the first to seventh items, the biometric data may include third information indicating pits and bumps of a feature portion of the user.

In the identifying device according to one of the first to seventh items, the biometric data may include fourth information indicating a shape of a feature portion of the user.

In the identifying device according to one of the first to seventh items, the biometric data may include fifth information indicating a position of a feature portion of the user.

[Item 9]

In the identifying device according to the eighth item, the processor may cause the image sensor to output a third signal indicating two-dimensional distribution of distances between the image sensor and a surface of the user, and may verify information obtained from the third signal against the third information to identify the user.

[Item 10]

In the identifying device according to the ninth item, the processor may cause the image sensor to detect a component of at least part of the reflected pulsed light in a rising period, the rising period being a period from start to end of an increase of an intensity of the reflected pulsed light, and may calculate the two-dimensional distribution of the distances, based on the component.

[Item 11]

An identifying device according to an 11th item includes a light source; an image sensor; a memory that stores therein biometric data indicating a feature of a body of a user; and a processor. The biometric data may include first information indicating texture of a skin surface of the user. The processor may cause the light source to emit illumination light with which a two-dimensional pattern including at least one bright portion and at least one dark portion is projected to the user, may cause the image sensor to detect at least part of reflected light that returns from the user and to output a signal corresponding to two-dimensional distribution of an intensity of the at least part of the reflected light, and may verify the signal against the biometric data stored in the memory to identify the user.

[Item 12]

In the identifying device according to the 11th item, the biometric data may further include second information indicating distribution of blood vessels of the user.

[Item 13]

In the identifying device according to the 12th item, the processor may cause the image sensor to detect at least part of first reflected light that returns from the at least one dark portion on the user to which the two-dimensional pattern is projected and to output a first signal corresponding to two-dimensional distribution of an intensity of the at least part of the first reflected light, and may verify information obtained from the first signal against the second information to identify the user.

[Item 14]

In the identifying device according to the 13th item, the processor may cause the image sensor to detect at least part of second reflected light that returns from the at least one bright portion on the user to which the two-dimensional pattern is projected and to output a second signal corresponding to two-dimensional distribution of an intensity of the at least part of the second reflected light, and may verify information obtained by subtracting the first signal from the second signal against the first information to identify the user.

[Item 15]

In the identifying device according to the 11th item, the processor may cause the image sensor to detect at least part of first reflected light that returns from the at least one dark portion on the user to which the two-dimensional pattern is projected, to detect at least part of second reflected light that returns from the at least one bright portion on the user, to output a first signal corresponding to two-dimensional distribution of an intensity of the at least part of the first reflected light, and to output a second signal corresponding to two-dimensional distribution of an intensity of the at least part of the second reflected light, and may verify information obtained by subtracting the first signal from the second signal against the first information to identify the user.

[Item 16]

In the identifying device according to the 11th item, the illumination light may be pulsed light.

[Item 17]

In the identifying device according to the 16th item, a pulse duration of the pulsed light may be more than or equal to 3 ns and less than or equal to 50 ns.

[Item 18]

In the identifying device according to the 16th or 17th item, the image sensor may include pixels; the processor may cause the image sensor to repeatedly accumulate charges in each of the pixels a thousand times to a hundred thousand times, the charges corresponding to the intensity of the at least part of the reflected light; and the signal may indicate two-dimensional distribution of a total amount of the charges accumulated in the pixels.

[Item 19]

In the identifying device according to the 16th or 18th item, the biometric data may further include third information indicating pits and bumps of a feature portion of the user.

[Item 20]

In the identifying device according to the 19th item, the processor may cause the image sensor to detect at least part of first reflected pulsed light that returns from the at least one dark portion on the user to which the two-dimensional pattern is projected, to detect at least part of second reflected pulsed light that returns from the at least one bright portion on the user, to output a first signal corresponding to two-dimensional distribution of an intensity of the at least part of the first reflected pulsed light, and to output a second signal corresponding to two-dimensional distribution of an intensity of the at least part of the second reflected pulsed light, and may verify information obtained by subtracting the first signal from the second signal against the third information to identify the user.

[Item 21]

In the identifying device according to one of the 16th to 18th items, the biometric data may further include second information indicating distribution of blood vessels of the user.

[Item 22]

In the identifying device according to the 21st item, the processor may cause the image sensor to detect at least part of first reflected pulsed light in a falling period and to output a first signal corresponding to two-dimensional distribution of an intensity of the at least part of the first reflected pulsed light in the falling period, the first reflected pulsed light returning from the at least one dark portion on the user to which the two-dimensional pattern is projected, and the falling period being a period from start to end of a decrease of an intensity of the first reflected pulsed light, and may verify information obtained from the first signal against the second information to identify the user.

[Item 23]

In the identifying device according to one of the 16th to 18th items, the processor may cause the image sensor to detect at least part of second reflected pulsed light in a rising period and to output a second signal corresponding to two-dimensional distribution of an intensity of the at least part of the second reflected pulsed light in the rising period, the second reflected pulsed light returning from the at least one bright portion on the user to which the two-dimensional pattern is projected, and the rising period being a period from start to end of an increase of an intensity of the second reflected pulsed light, and may verify information obtained from the second signal against the first information to identify the user.

[Item 24]

An identifying method according to a 24th item is an identifying method using an identifying device including a light source and an image sensor. The identifying method includes: causing the light source to emit pulsed light having a pulse duration of more than or equal to 0.2 ns and less than or equal to 1 µs to illuminate a user; causing the image sensor to detect at least part of reflected pulsed light that returns from the user and to output a signal corresponding to two-dimensional distribution of an intensity of the at least part of the reflected pulsed light; and verifying the signal against biometric data indicating a feature of a body of the user to identify the user.

[Item 25]

An identifying method according to a 25th item is an identifying method using an identifying device including a light source and an image sensor. The identifying method includes: causing the light source to emit illumination light with which a two-dimensional pattern including at least one bright portion and at least one dark portion is projected to the user; causing the image sensor to detect at least part of reflected light that returns from the user and to output a signal corresponding to two-dimensional distribution of an intensity of the at least part of the reflected light; and verifying the signal against biometric data indicating texture of a skin surface of the user to identify the user.

What is claimed is:

1. An identifying device comprising:
   a light source;
   an image sensor;
   a memory that stores biometric data indicating a feature of a body of a user; and
   a processor that
      causes the light source to emit illumination light with which a two-dimensional pattern including at least one bright portion and at least one dark portion is projected to the user,
      causes the image sensor to detect at least part of first reflected light that returns from the at least one dark portion on the user to which the two-dimensional pattern is projected, to detect at least part of second reflected light that returns from the at least one bright portion on the user, to output a first signal corresponding to two-dimensional distribution of an intensity of the at least part of the first reflected light, and to output a second signal corresponding to two-dimensional distribution of an intensity of the at least part of the second reflected light,
      obtains information by subtracting the first signal from the second signal, and
      verifies the information against the biometric data to identify the user.

2. The identifying device according to claim 1, wherein the illumination light is pulsed light.

3. The identifying device according to claim 2, wherein a pulse duration of the pulsed light is more than or equal to 3 ns and less than or equal to 50 ns.

4. The identifying device according to claim 2, wherein the image sensor includes pixels,
   the processor causes the image sensor to repeatedly accumulate charges in each of the pixels a thousand times to a hundred thousand times, the charges corresponding to the intensity of the at least part of the reflected light, and
   each of the first signal and the second signal indicates two-dimensional distribution of a total amount of the charges accumulated in the pixels.

5. The identifying device according to claim 2, wherein the biometric data further includes unevenness information indicating pits and bumps of at least one of an orbit, a nose, a cheek, a cheekbone, a mouth, a jaw, a chin, and a part below an ear of the user.

6. The identifying device according to claim 5, wherein the processor
   verifies the information obtained by subtracting the first signal from the second signal against the unevenness information to identify the user.

7. The identifying device according to claim 2, wherein the biometric data further includes blood vessel information indicating distribution of blood vessels of the user.

8. The identifying device according to claim 7, wherein the processor
   verifies information obtained from the first signal against the blood vessel information to identify the user.

9. The identifying device according to claim 2, wherein the processor
   verifies information obtained from the second signal against the skin texture information to identify the user.

10. An identifying method using an identifying device including a light source and an image sensor, the identifying method comprising:
   causing the light source to emit illumination light with which a two-dimensional pattern including at least one bright portion and at least one dark portion is projected to the user;
   causing the image sensor to detect at least part of first reflected light that returns from the at least one dark portion on the user to which the two-dimensional pattern is projected, to detect at least part of second reflected light that returns from the at least one bright portion on the user, to output a first signal corresponding to two-dimensional distribution of an intensity of the at least part of the reflected light, and to output a second signal corresponding to two-dimensional distribution of an intensity of the at least part of the second reflected light;
   obtaining information by subtracting the first signal from the second signal, and
   verifying the information against biometric data indicating a feature of a body of the user, to identify the user.

* * * * *